(12) United States Patent
Steensen et al.

(10) Patent No.: US 11,246,603 B2
(45) Date of Patent: Feb. 15, 2022

(54) DUAL STYLUS VARIABLE ANGLE TOTAL KNEE INSTRUMENTS AND METHODS

(71) Applicant: MicroPort Orthopedics, Inc., Arlington, TN (US)

(72) Inventors: Robert N. Steensen, Hilliard, OH (US); Brian R. Harris, Cordova, TN (US); Jeff R. Justis, Germantown, TN (US)

(*) Notice: Subject to any disclaimer, the term of this patent is extended or adjusted under 35 U.S.C. 154(b) by 0 days.

(21) Appl. No.: 16/258,340

(22) Filed: Jan. 25, 2019

(65) Prior Publication Data
US 2019/0231365 A1    Aug. 1, 2019

Related U.S. Application Data

(60) Provisional application No. 62/622,576, filed on Jan. 26, 2018.

(51) Int. Cl.
*A61B 17/15* (2006.01)
*A61B 17/17* (2006.01)
*A61B 90/00* (2016.01)

(52) U.S. Cl.
CPC .......... *A61B 17/155* (2013.01); *A61B 17/157* (2013.01); *A61B 17/1764* (2013.01); *A61B 2090/033* (2016.02); *A61B 2090/036* (2016.02); *A61B 2090/067* (2016.02)

(58) Field of Classification Search
CPC ... A61B 17/155; A61B 17/157; A61B 5/4528; A61B 17/025; A61B 2017/0268; A61B 17/1764; A61B 17/8866
See application file for complete search history.

(56) References Cited

U.S. PATENT DOCUMENTS

| 5,578,039 A | * | 11/1996 | Vendrely | A61B 17/157 606/88 |
| 6,013,081 A | | 1/2000 | Burkinshaw et al. | |
| 6,059,788 A | * | 5/2000 | Katz | A61B 17/155 606/102 |

(Continued)

FOREIGN PATENT DOCUMENTS

WO    WO2013057514 A1    4/2013

OTHER PUBLICATIONS

Wright Medical Technology, Inc. Evolution Medial-Pivot Knee System Surgical Technique, Distal Cut First, Jul. 7, 2013, pp. 1-48, Arlington, TN, USA.

*Primary Examiner* — Kevin T Truong
*Assistant Examiner* — Lisa Nguyen
(74) *Attorney, Agent, or Firm* — Robert J. Hornung

(57) ABSTRACT

An instrument for setting a position of a resection of a distal femur or a proximal tibia in a total knee arthroplasty, the instrument comprising: a stable portion, the stable portion configured for orientation in a set position relative to said distal femur or said proximal tibia; a resection guide portion, the resection guide portion configured to guide a resection path for said resection; a resection guide body, the resection guide body associated with the resection guide portion in a fixed orientation; the resection guide body pivotally connected to the stable portion, whereby pivoting adjustment of the resection guide body on the stable portion sets a resection orientation of the resection guide portion; and the resection guide body having a lock for selectively locking the resection guide body to the stable portion at a plurality of selectable resection orientations.

6 Claims, 30 Drawing Sheets

(56) References Cited

U.S. PATENT DOCUMENTS

| | | |
|---|---|---|
| 6,458,135 B1 | 10/2002 | Harwin et al. |
| 7,374,563 B2 | 5/2008 | Roger et al. |
| 7,686,812 B2 | 3/2010 | Axelson, Jr. et al. |
| 7,794,467 B2 | 9/2010 | McGinley et al. |
| 8,425,524 B2 | 4/2013 | Aker et al. |
| 8,444,651 B2 | 5/2013 | Kunz et al. |
| 8,591,516 B2 | 11/2013 | Metzger et al. |
| 8,672,945 B2 | 3/2014 | Lavallee et al. |
| 8,734,453 B2 | 5/2014 | Tuttle et al. |
| 8,740,910 B2 | 6/2014 | McMillen et al. |
| 8,974,459 B1 | 3/2015 | Axelson, Jr. et al. |
| 9,113,957 B2 | 8/2015 | Axelson, Jr. et al. |
| 9,855,057 B2 | 1/2018 | Axelson, Jr. et al. |
| 10,130,375 B2 | 11/2018 | Yager et al. |
| 2007/0173851 A1 | 7/2007 | McMillen et al. |
| 2008/0161815 A1 | 7/2008 | Schoenefeld et al. |
| 2010/0121334 A1 | 5/2010 | Couture et al. |
| 2010/0217338 A1 | 8/2010 | Carroll et al. |
| 2010/0268240 A1* | 10/2010 | Mc Ginley .......... A61B 17/155 606/88 |
| 2017/0238946 A1* | 8/2017 | van der Walt ......... A61B 34/20 |
| 2019/0046215 A1 | 2/2019 | Yager et al. |

\* cited by examiner

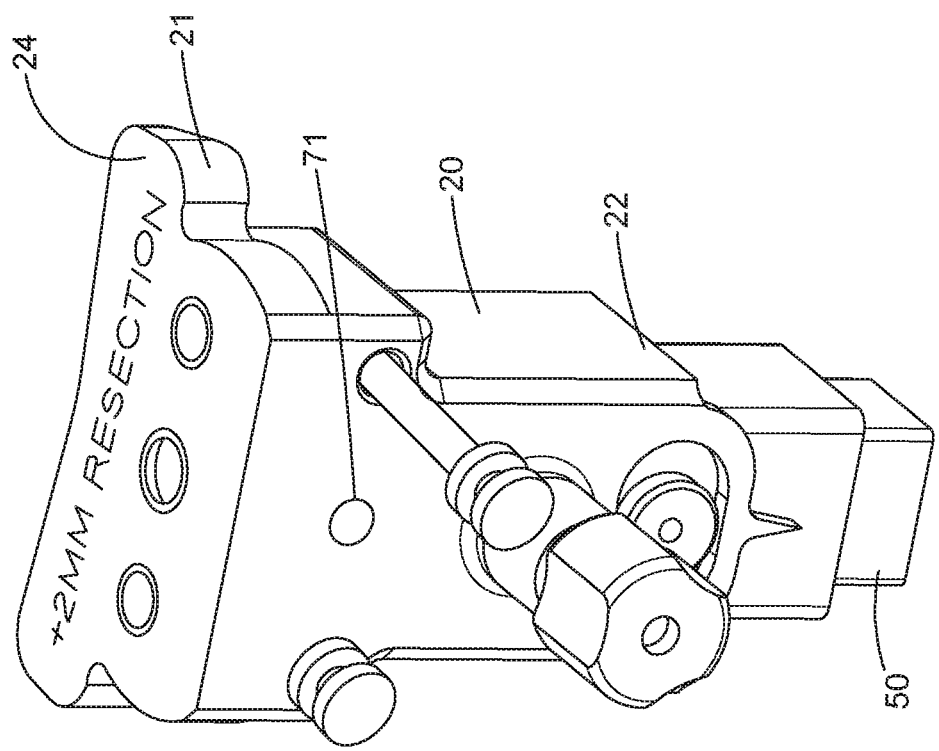

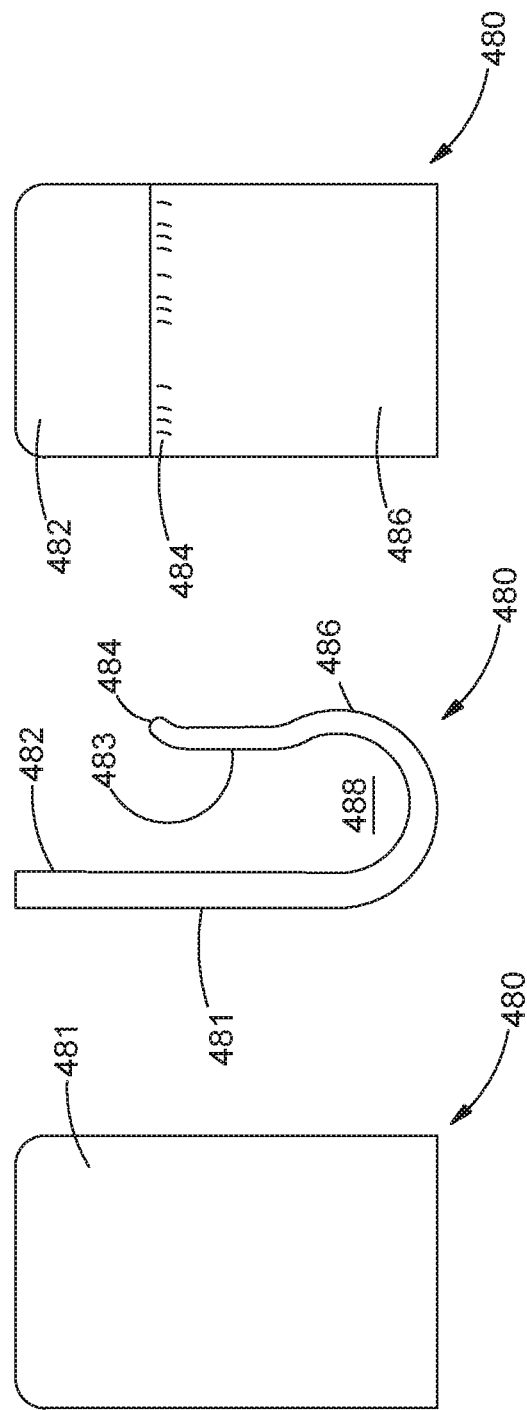

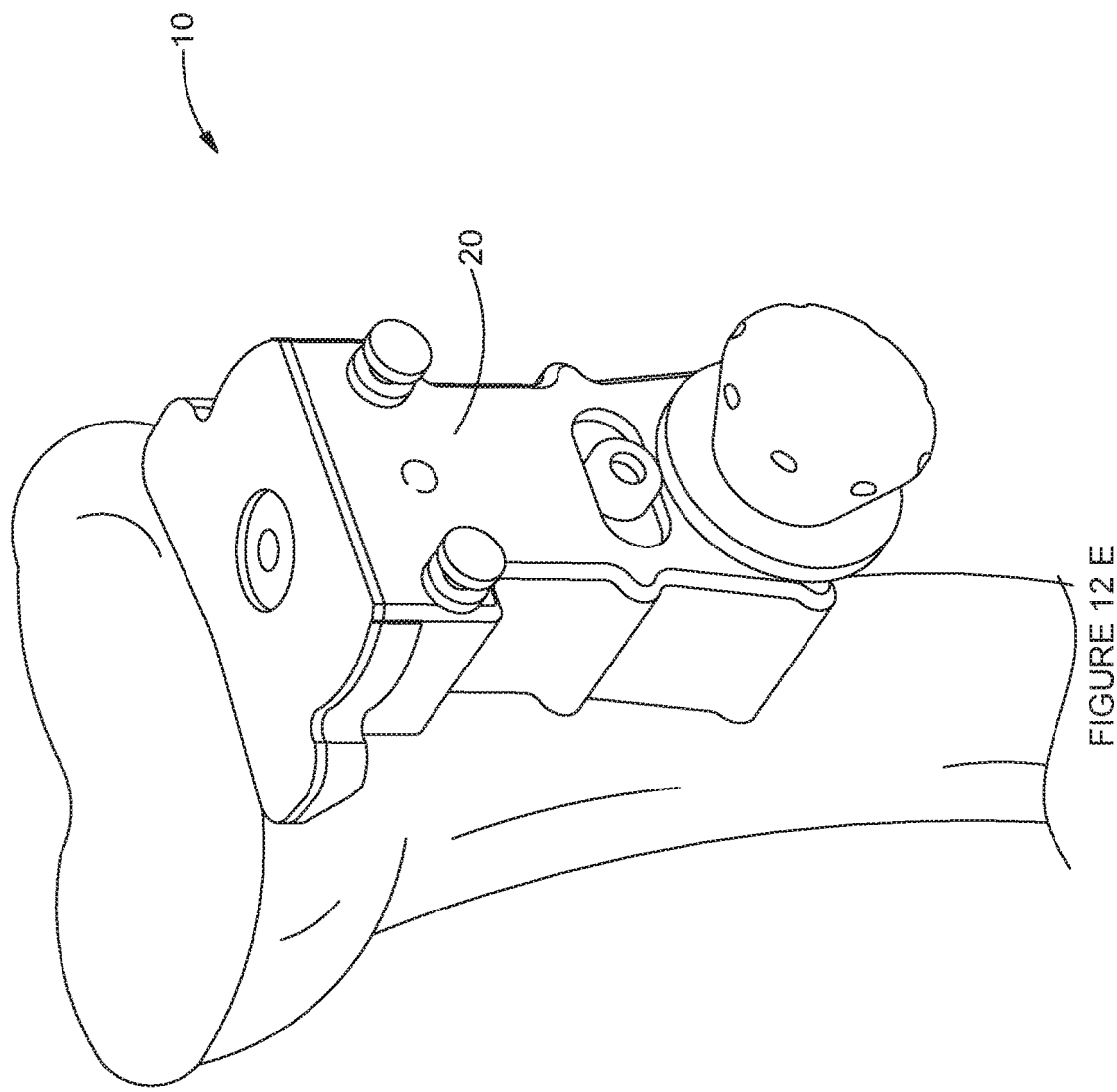

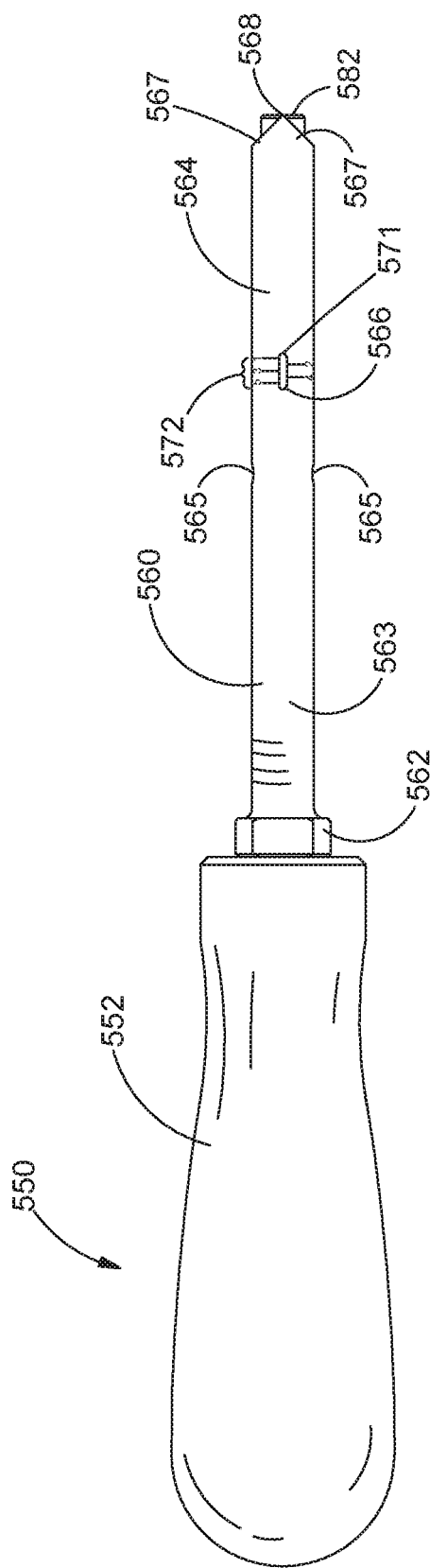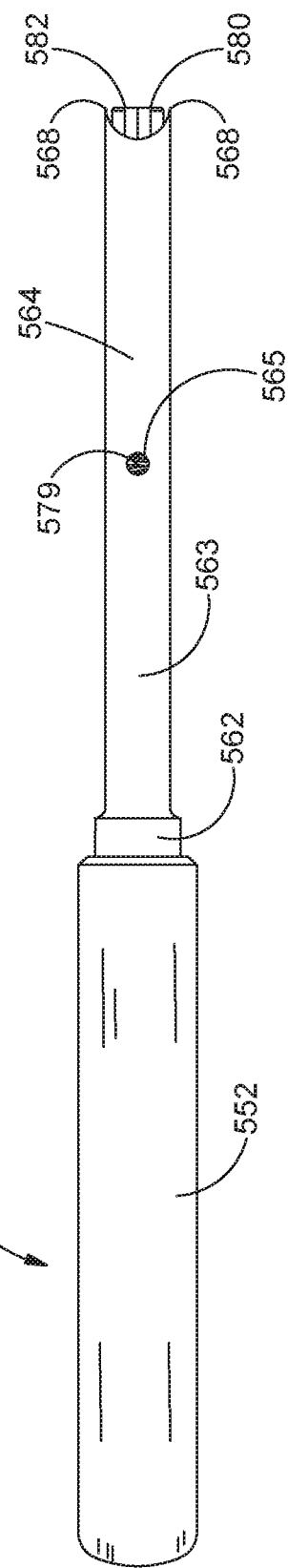
FIGURE 14 A
FIGURE 14 B

DUAL STYLUS VARIABLE ANGLE TOTAL KNEE INSTRUMENTS AND METHODS

CROSS REFERENCE TO RELATED APPLICATIONS

This application claims the benefit of U.S. Provisional Patent Application 62/622,576, filed Jan. 26, 2018.

STATEMENT REGARDING FEDERALLY SPONSORED RESEARCH

Not applicable

FIELD OF THE INVENTION

The present invention relates to orthopedic surgery of the knee, and more particularly to total knee implantation instruments and methods.

BACKGROUND OF THE INVENTION

During knee arthroplasty, a surgeon resects existing bone and cartilage to shape the femur and tibia for resurfacing with knee implant components. Various instrument designs have been proposed for resecting the knee. Some resection systems include options for balancing the ligaments of the knee for better functioning of the knee implant, in what is commonly called "gap balancing" technique. Other systems resect a specific amount of bone from the surface, in what is commonly called "measured resection" technique.

There are three alignment goals a surgeon can strive to achieve: Mechanical, Anatomic, and Kinematic. Most commonly used is mechanical alignment. The priority in mechanical alignment is to resect the tibia perpendicular to the length or axis of the tibial shaft. The resections of the femur are adjusted to account for this, and any necessary ligament releases are performed. Anatomic alignment tries to resect the tibia at 3 degrees of varus, and femoral resections and ligament releases are performed to keep a straight hip-knee-ankle axis of the limb. The goal of kinematic alignment is to implant the knee component surfaces at the natural joint surface level present prior to the development of arthritis.

Existing knee resection and ligament balancing instruments suffer from a number of drawbacks. For example, existing systems do not provide for some or all of the following features: allow the angle of the current or natural joint surface to be measured on both the femur and tibia; allow a wear factor to be used so that the bone resection restores the joint surface to its pre-arthritic level on both the femur and tibia; allow the surgeon to resect a specific amount of bone from medial and lateral aspects of the joint surface on both the femur and tibia and visualize the angle of resection; allow the angle of resection to float infinitely, rather than in specific increments, within an acceptable range on both the femur and tibia; and allow the surgeon to selectively lock the angle if desired and measure the resection of medial and lateral femoral condyles or of the medial and lateral tibial plateau.

It would therefore be unique and advantageous to have instruments that measure medial and lateral resections and the angle of resection on both the femur and tibia having the characteristics and features described herein.

OBJECTS AND SUMMARY OF THE INVENTION

It is an object of the invention to provide knee resection instruments and methods that allow the angle of the current joint surface to be measured on both the femur and tibia.

It is another object of the invention to provide knee resection instruments and methods that allow a wear factor to be used so that the bone resection restores the joint surface to its pre-arthritic level on both the femur and tibia.

It is another object of the invention to provide knee resection instruments and methods that allow the surgeon to resect a specific amount of bone from medial and lateral aspects of the joint surface on both the femur and tibia and visualize the angle of resection.

It is another object of the invention to provide knee resection instruments and methods that allow the angle of resection to float infinitely, rather than in specific increments, within an acceptable range on both the femur and tibia.

It is yet another object of the invention to provide knee resection instruments and methods that allow the surgeon to selectively lock the angle if desired and measure the resection of medial and lateral femoral condyles or of the medial and lateral tibial plateau.

The foregoing objectives are achieved by providing knee resection and ligament balancing instruments having the features described herein.

The inventions include an instrument for setting a position of a resection of a distal femur or a proximal tibia in a total knee arthroplasty, the instrument comprising: a stable portion, the stable portion configured for orientation in a set position relative to said distal femur or said proximal tibia; a resection guide portion, the resection guide portion configured to guide a resection path for said resection; a resection guide body, the resection guide body associated with the resection guide portion in a fixed orientation; the resection guide body pivotally connected to the stable portion, whereby pivoting adjustment of the resection guide body on the stable portion sets a resection orientation of the resection guide portion; and the resection guide body having a lock for selectively locking the resection guide body to the stable portion at a plurality of selectable resection orientations.

In embodiments, the instrument is configured for resection of said distal femur. In embodiments, the stable portion is oriented in the set position by securing the stable portion on an intramedullary rod extending from said distal femur. The resection path can be provided by a resection slot in the resection guide portion, the resection guide portion configured for fixation to the distal femur and selective detachment from the resection guide body. Selective detachment of the resection guide portion is provided by a release button on the resection guide body.

In embodiments, the resection guide body has a medial adjustment pad and a lateral adjustment pad, each adjustment pad selectively adjustable against said femur to pivot the resection guide body on the stable portion to thereby set the resection guide portion in to a resection orientation. A gauge can be provided for measuring a resection orientation, the gauge comprising the stable portion having a degree scale and the resection guide body having a pointer overlaying the degree scale.

In embodiments, the instrument is configured for resection of said proximal tibia. In tibial embodiments, the stable portion can be oriented in the set position by securing the stable portion on an extramedullary tibial alignment instrument. The resection path can be provided by a planar resection surface on a proximal end of the resection guide portion.

In embodiments, an adjustable double tibial stylus removably mounted on a proximal end of the resection guide body, the adjustable double tibial stylus having a lateral stylus member and a medial stylus member, each stylus member adjustable against said tibia to pivot the resection guide body on the stable portion to thereby set the resection guide portion in a resection orientation, each stylus member further adjustable in an anterior-posterior dimension. A gauge can be provided for measuring a resection orientation, the gauge comprising the stable portion having a degree scale and the resection guide body having a pointer overlaying the degree scale.

In embodiments, the plurality of selectable resection orientations are indiscrete locations within a working range of resection orientations. In other embodiments, the plurality of selectable resection orientations are discrete locations. In embodiments, the plurality of selectable resection orientations are indicted by a gauge arrangement. The gauge arrangement may comprise a pointer on a distal end of the resection guide body and an adjacent degree scale on the stable portion. The degree scale can be discrete degree markings over a working range. The working range can include discrete degree markings at −4, −3, −2, −1, 0, 1, 2, 3 and 4 degrees.

Other instruments, such as a cartilage thickness gauge and a gap space gauge, are included and described herein. The invention further includes methods of using the foregoing instruments and variations thereof in surgical procedures, which are described herein.

The foregoing and other objects, features, aspects, and advantages of the invention will become more apparent from the following detailed description of the invention when considered in conjunction with the accompanying drawings.

BRIEF DESCRIPTION OF THE DRAWINGS

FIG. 2B is a front-top perspective view of one embodiment of an adjustable extramedullary tibial resection guide of the invention, configured for use in a plus resection.

FIG. 9A is a side view of one embodiment of a clip-on spacer of the invention.

FIG. 9B is a proximal side view of one embodiment of a clip-on spacer of the invention.

FIG. 9C is a distal side view of one embodiment of a clip-on spacer of the invention.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Instrument Assembly

Figure 1:
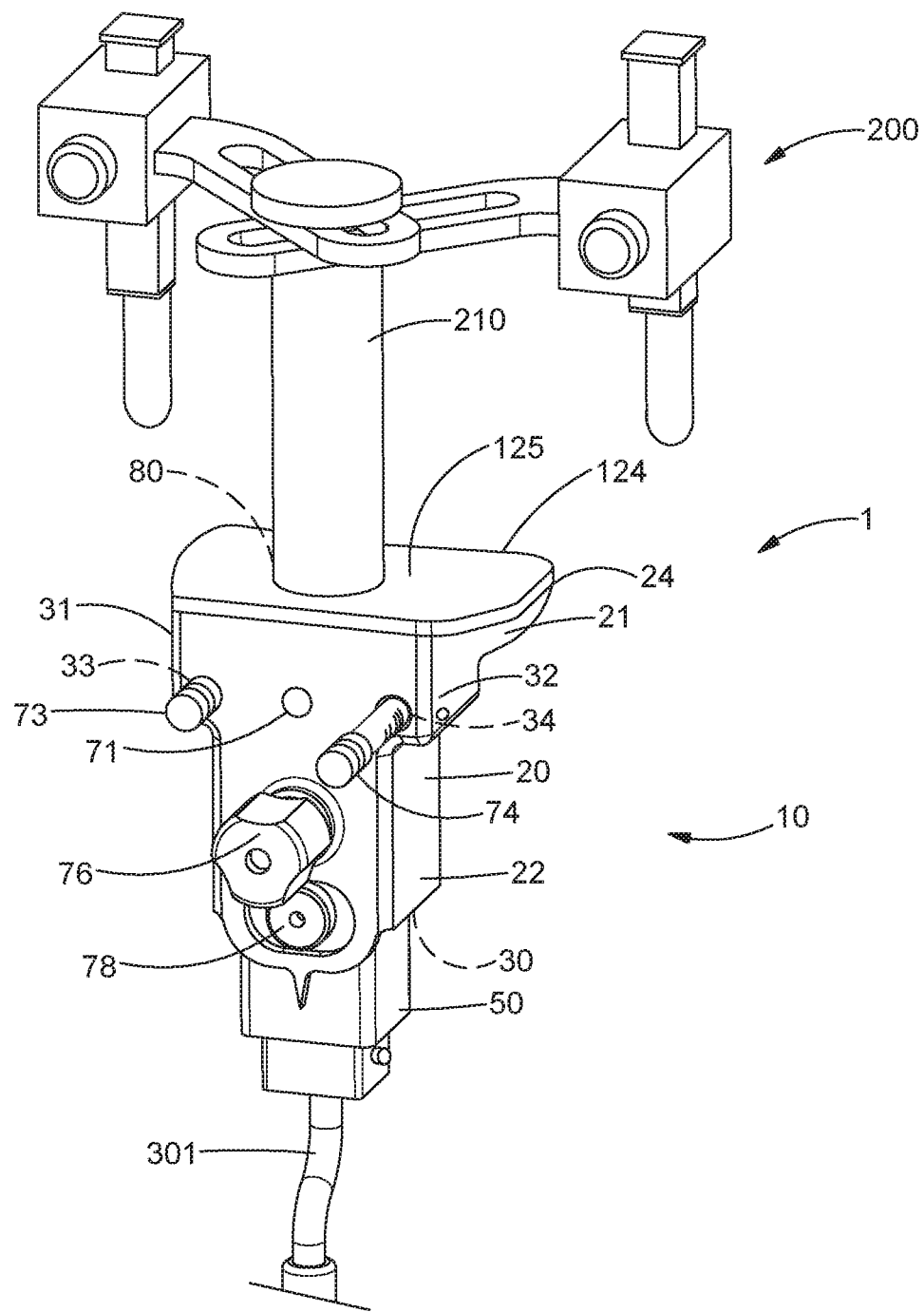
FIG. 1 is a front-side perspective view of one embodiment of an instrument assembly of the invention, featuring an adjustable double tibial stylus functionally attached to an adjustable extramedullary tibial resection guide.
Figure 2A:
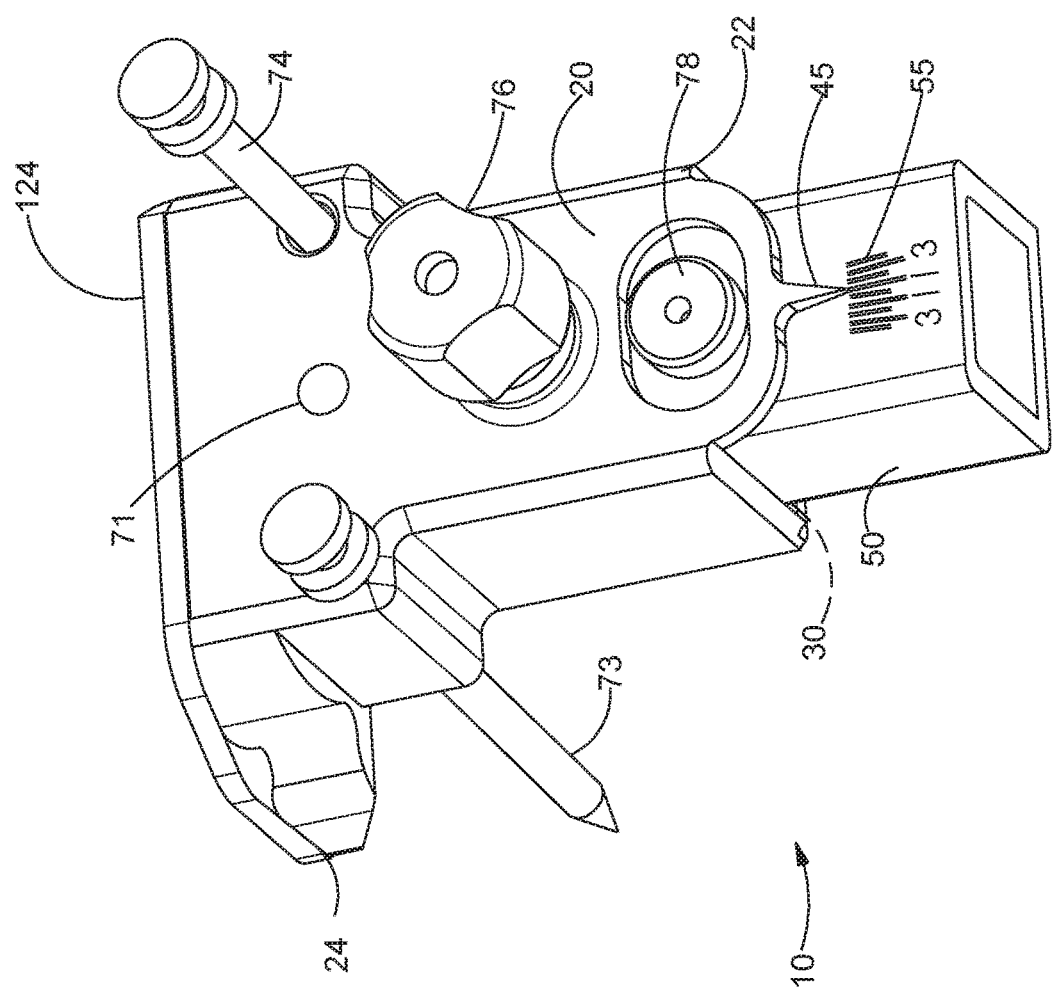
FIG. 2A is a front-side perspective view of one embodiment of an adjustable extramedullary tibial resection guide of the invention.

As shown in FIG. 1, the invention includes, generally, an instrument assembly 1 having an adjustable double tibial stylus 200 functionally mounted on a proximal end 21 of an adjustable extramedullary tibial resection guide 10, such as by insertion of a tubular body member 210 of the adjustable double tibial stylus 200 into a proximal bore 80 formed in the proximal end 21 of the tibial resection guide 10. As indicated in FIG. 2A, the tibial stylus 200 is selectively removable from the tibial resection guide 10, such as during resection, as well as during storage and cleaning of the instruments.

Adjustable Tibial Resection Guide

Details of the adjustable tibial resection guide 10 will now be described with reference to FIGS. 1 and 2A-2C. The tibial resection guide 10 includes, generally, a tibial resection guide body 20 pivotally attached to a stable portion 50, such as a tibial guide support member 50. The tibial resection guide body 20 has a proximal end 21 and a distal end 22. In the embodiment depicted in FIG. 1, a proximal end of the tibial support member 50 is disposed in an internal receptacle 30 of the tibial resection guide body 20. As indicated in FIGS. 2A and 2B, the tibial resection guide body 20 is secured to the tibial support member 50 in a varus/valgus pivotal arrangement, such as by front hinge pin 71 and back hinge pin 72. As will be described in further detail herein, in this manner the tibial resection guide body 20 may be selectively rotated or dialed to a selected varus/valgus angle. As shown in FIG. 2A, the selected varus/valgus angle may be indicted by a gauge arrangement, such as a pointer 45 formed on a distal end of the tibial resection guide body 20 and an adjacent degree scale 55 etched or otherwise affixed to a distal area of the body of the tibial support member 50. The degree scale 55 may include discrete degree markings over a working range, such as −4, −3, −2, −1, 0, 1, 2, 3 and 4. In some exemplary embodiments, this mechanical method of confirming the angle of the device might be replaced or assisted by one or more electronic guidance device(s). For example, an electronic guidance device of the type currently offered by OrthAlign could be coupled to the tibial resection guide 10 to electronically confirm the angle of the cutting surface is properly set. The adjustability of the instruments of the present invention could enhance and improve ease of use of such electronic devices.

The tibial resection guide 10 may be configured to free float the varus/valgus angle. Alternatively, the tibial resection guide 10 may be configured to dial adjust the angle in specific increments. Various mechanisms can be used for the dial adjuster, such as a cam drive or a threaded drive. A threaded drive allows for finer control of the angle selection.

As indicated in FIG. 2B, a tibial resection surface 24 is provided or formed on the proximal surface of the proximal end 21. As shown in FIG. 1, a tibial resection spacer 124 is provided to overlay the tibal resection surface 24. In the depicted embodiment, the tibial resection body 20 is sized such that the tibial resection guide surface 24 is spaced to provide an undercut resection, such as a minus 2 mm resection. The tibial resection spacer 124 is sized to provide a neutral tibial resection. An outer profile of the tibial resection spacer 124 generally matches or closely matches the outer profile of the tibial resection surface 24.

FIG. 1 also illustrates how left and right medial extensions 31, 32 may be formed on the proximal end 21 of the tibial resection guide body 20. In addition to providing support for the resection surface 24, the left and right medial extensions 31, 32 may be provided with respective left and right medial spike pin bores 33, 34. Each of the spike pin bores 33, 34 is sized to closely receive a spike pin 73, 74 for use in selectively securing the resection guide 10 to a proximal femur of a patient for use in making a tibial resection.

A mechanism is provided for selectively locking the tibial resection guide 10 at a selected varus/valgus angle. In the embodiment of FIG. 1, the locking arrangement includes a lock knob 76 secured in the tibial guide support member 50 through a bore 36 in tibial resection guide body 20. When a desired varus/valgus angle is obtained, the surgeon tightens the lock knob 76 until the tibial resection guide 10 is fixedly positioned relative to the tibial guide support member 50.

Figure 2C:
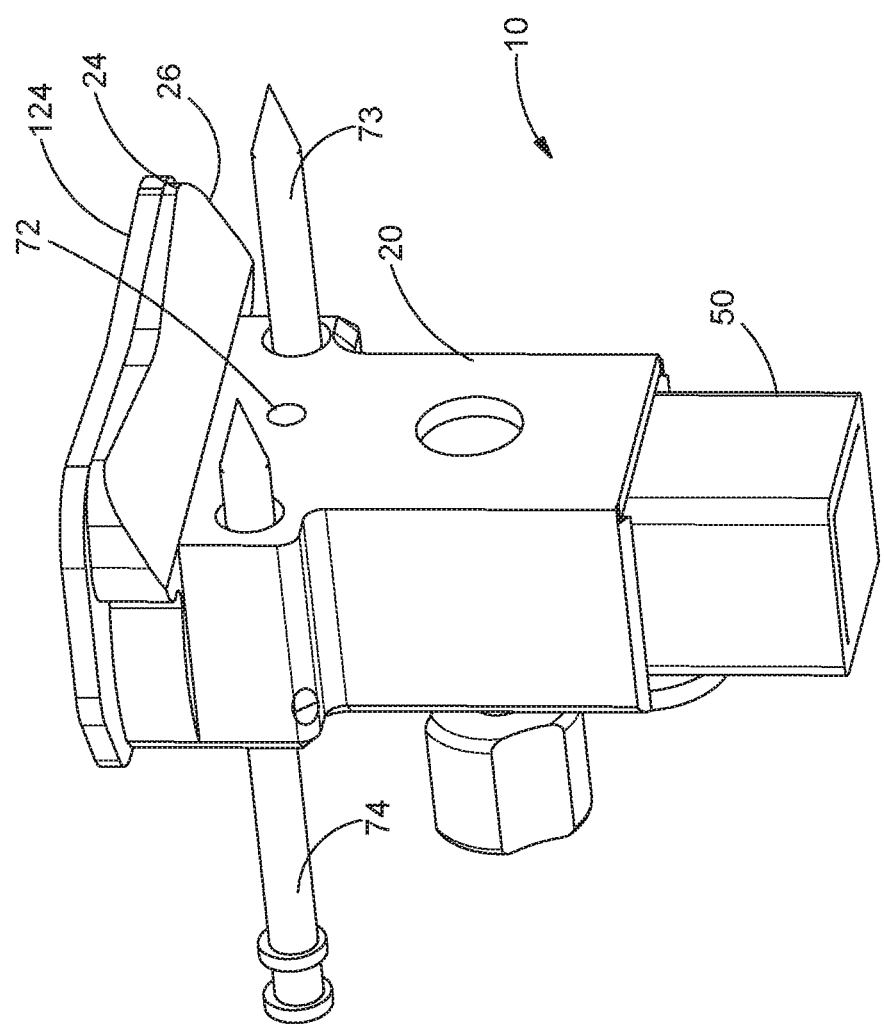
FIG. 2C is a back-side perspective view of an adjustable extramedullary tibial resection guide of the invention.

FIG. 2C shows a side-distal perspective of the tibial resection guide 10. Spike pins 73, 74 are shown extending posteriorly from the guide body 20 for use in securing the instrument to a proximal tibia of a patient. A posterior extension 26 of the tibial resection surface 24 is shown.

Figure 5:
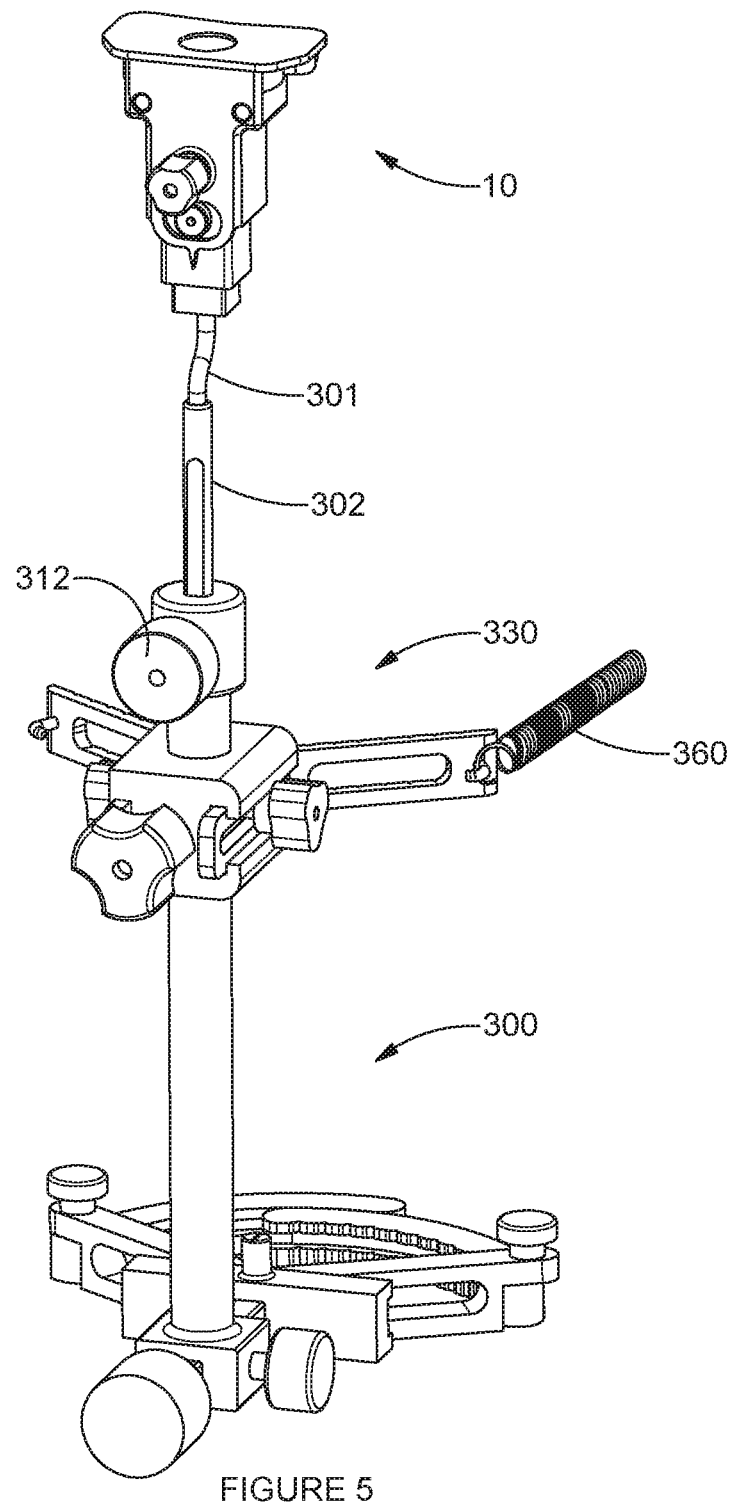
FIG. 5 is a front-side perspective view of one embodiment of an adjustable extramedullary tibial resection guide functionally attached to a proximal end of an extramedullary tibial alignment instrument.

As shown in FIG. 1, the tibial guide support member 50 is configured to attach to a tibial alignment guide attachment member 301. As shown in FIG. 5, the tibial alignment guide attachment member 301 is configured to further attach to an extramedullary tibial alignment instrument 300. The tibial alignment guide attachment member 301 could be adapted to attach to an intramedullary tibial alignment instrument depending on the preferences of the user.

Figure 8:
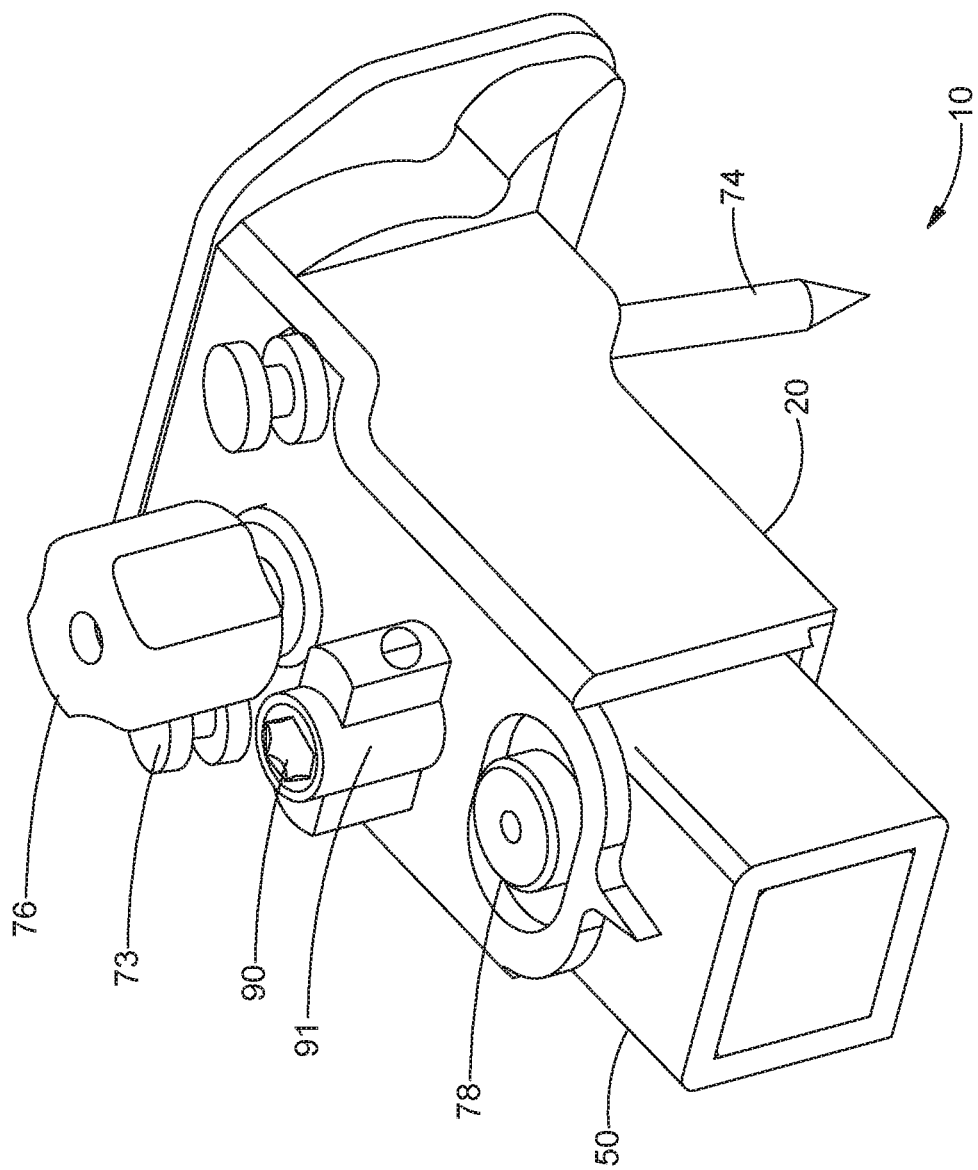
FIG. 8 is a front-side perspective view of one embodiment of an adjustable extramedullary tibial resection guide of the invention featuring locking camming adjustment mechanism.

FIG. 8 is a front-side perspective view of one embodiment of an adjustable extramedullary tibial resection guide 10 of the invention featuring a camming adjustment mechanism. The configuration of the embodiment shown in FIG. 8 is similar to the embodiment of FIG. 2A, but additionally features a camming adjustment mechanism 90 for adjusting the varus-valgus angle. The camming adjustment mechanism 90 includes an outer adjustment member 91 configured for use in adjusting the camming adjustment mechanism. In the embodiment of FIG. 8, the adjustment member 91 is configured to rotate counter or counter-clockwise in a fixed position. While various mechanisms can be used to provide a camming adjustment, in one embodiment, the adjustment member 91 includes an off-center post formed on an interior end thereof, while the tibial guide support member 50 features a slot formed therein (not shown). The slot is sized and positioned to receive the off-center post therein in a camming relationship. In this manner, turning the adjustment member 91 left or right causes the off-center post to cam against the slot, adjusting the varus/valgus angle. The embodiment of FIG. 8 is configured to adjust to any varus-valgus position within the available range of motion. The knob 76 is configured for selective locking of the tibial support guide member 50 relative to the tibial resection guide body 20. Thus, once a desired varus/valgus angle is obtained, the surgeon can optionally lock the position via the knob 76.

Extended Tibial Resection

Figure 2D:
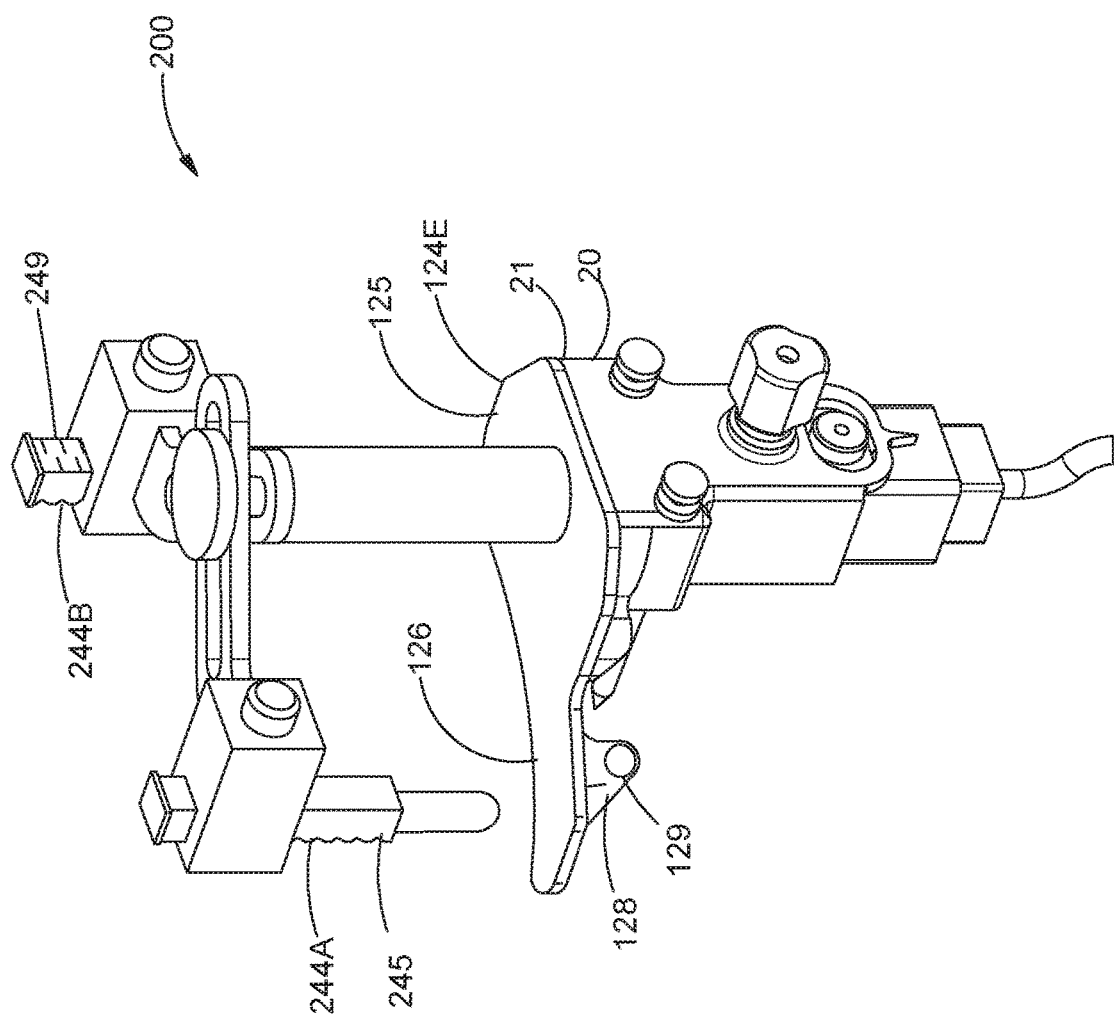
FIG. 2D is a front-side perspective view of one embodiment of an instrument assembly of the invention, featuring an extended resection guide functionally attached to an adjustable extramedullary tibial resection guide.

FIG. 2D provides a view of an extended tibial resection guide spacer 124E mounted on a proximal end 21 of a tibial resection guide body 20. A main tibial resection platform 125 of the extended tibial resection guide spacer 124E is similar or identical to the non-extended tibial resection spacer 124 shown in FIG. 1. However, the extended tibial resection spacer 124E includes an extension member 126 extending from a medial side thereof.

FIG. 2D shows a left knee embodiment of an extended tibial resection guide spacer 124E. A right knee embodiment of the tibial resection guide spacer 124E, while not shown in the drawings, would typically be configured as a mirror image of the left knee tibial resection guide spacer 124E.

Adjustable Double Tibial Stylus

Figure 3:
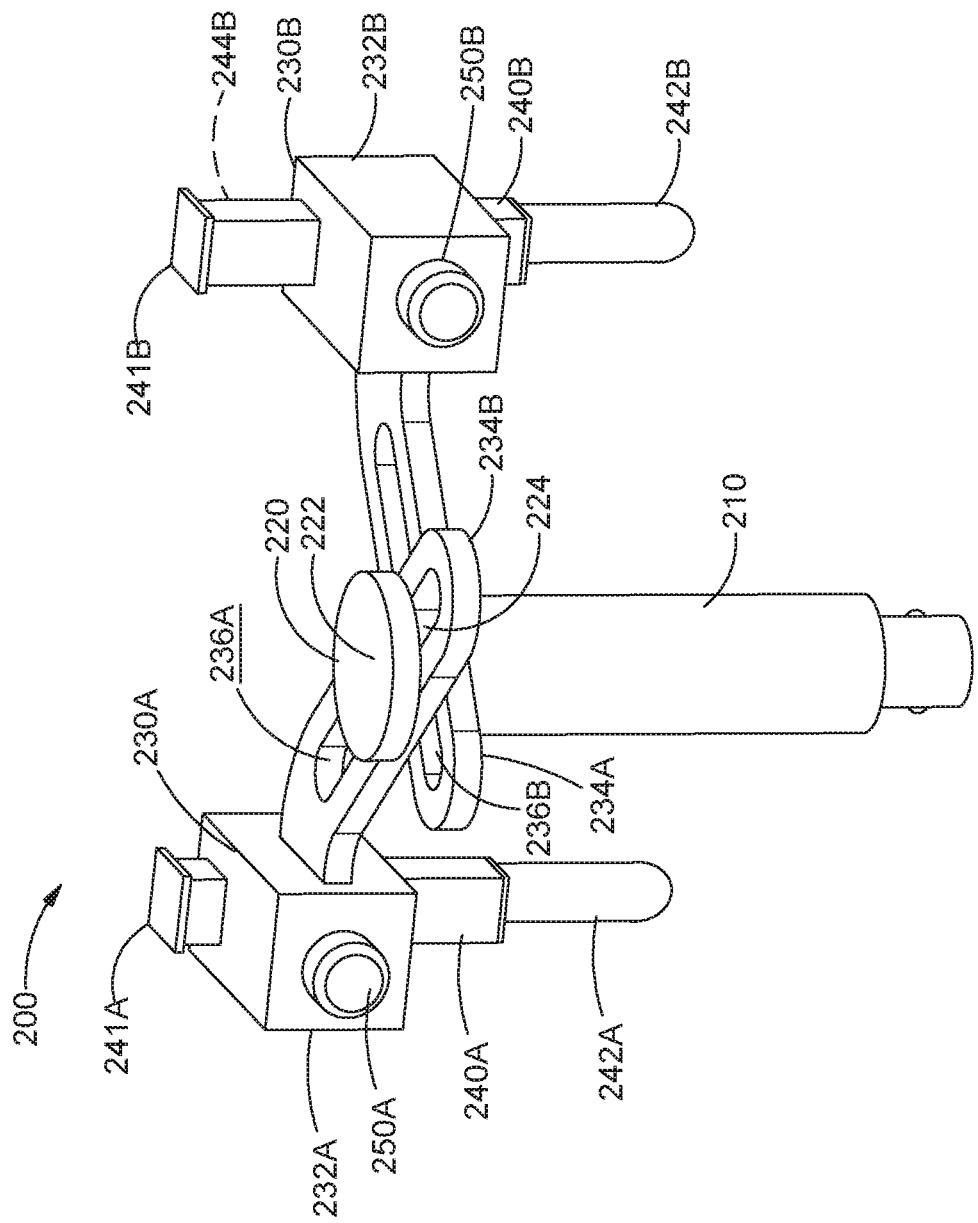
FIG. 3 is top-front perspective view of one embodiment of an adjustable double tibial stylus.

FIG. 3 shows one embodiment of an adjustable double tibial stylus 200 configured for use with the tibial resection guide 10. The adjustable double tibial stylus 200 includes first and second stylus members 230A, 230B arranged in a translating relationship relative to one another. In the embodiment shown in FIG. 3, the first and second stylus members 230A, 230B each include a first/second support member 232A, 232B, respectively. Each stylus support member 232A, 232B has a first/second stylus arm 234A, 234B, respectively, extending therefrom. Each stylus arm 234A, 234B has a first/second lengthwise groove 236A, 236B, respectively, formed therein.

In the embodiment of FIG. 3, the first and second stylus members 230A, 230B are substantially mirror images of one another. The first and second stylus members 230A, 230B are arranged on opposing sides of a generally centrally positioned tubular body member 210. A retaining post 220 extends proximally from the tubular body member 210. The retaining post 220 includes a proximal head 222 and an annular neck 224. The annular neck 224 is closely sized to fit within a width of the first and second annular grooves 236A, 236B. The annular neck 224 passes through the lengthwise grooves 236A, 236B of each of the first and second stylus arms 234A, 234B such that each stylus arm 234A, 234B pivots and translates about the post 210 while being retained on the post by the head 222.

Each of the first and second support members 232A, 232B includes a cavity for receiving a first/second adjustable tibial stylus member 240A, 240B therethrough in a substantially proximal-distal orientation. Each tibial stylus member 240A, 240B includes a first/second stop member 241A, 241B, respectively, on a proximal end thereof, and a first/second stylus tip 242A, 242B, respectively, on an opposing distal end thereof. The stylus tips 242A, 242B are configured to selectively abut a tibial articular surface of a patient during use of the instrument assembly 1. Each of the first and second tibial stylus members 240A, 240B is configured to translate proximally/distally within its respective support member 232A, 232B. Selective positioning of the tibial styluses 242A, 242B can be provided by a ratchet mechanism, with a plurality of ratchet teeth 244 formed on a ratchet portion 245. In the view of FIGS. 2D and 3, the rachet portion 245 positioned along a back or posterior side of the tibial stylus member 240 between the stop member 241 and the stylus tip 242. In the view of FIG. 2B, the ratchet teeth 244A of the second tibial stylus member 240A are visible on the back or posterior side of the tibial stylus instrument 200. A stylus button 250A, 250B is provided on each support member 232A, 232B. The stylus button 250A, 250B is operatively connected to the ratchet teeth 244, such that depressing the stylus button 250A, 250B releases the ratchet teeth 244 for selective repositioning of the tibial stylus member 240 relative to an articular surface of the tibial plateau of a patient. Release of the stylus button 250 locks the tibial stylus member 240A, 240B in position.

Figure 13:
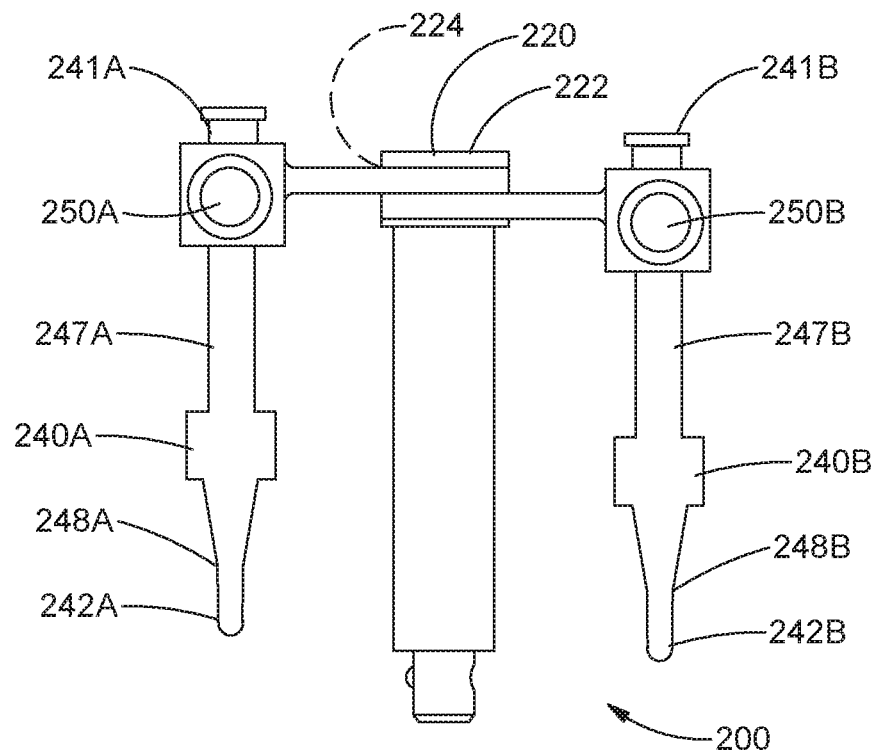
FIG. 13A is a rear/posterior view of one embodiment of an adjustable double tibial stylus.
FIG. 13B is a top view of the adjustable double tibial stylus of FIG. 13A.
FIG. 13C is a side view of the adjustable double tibial stylus of FIG. 13A.
Figure 13:
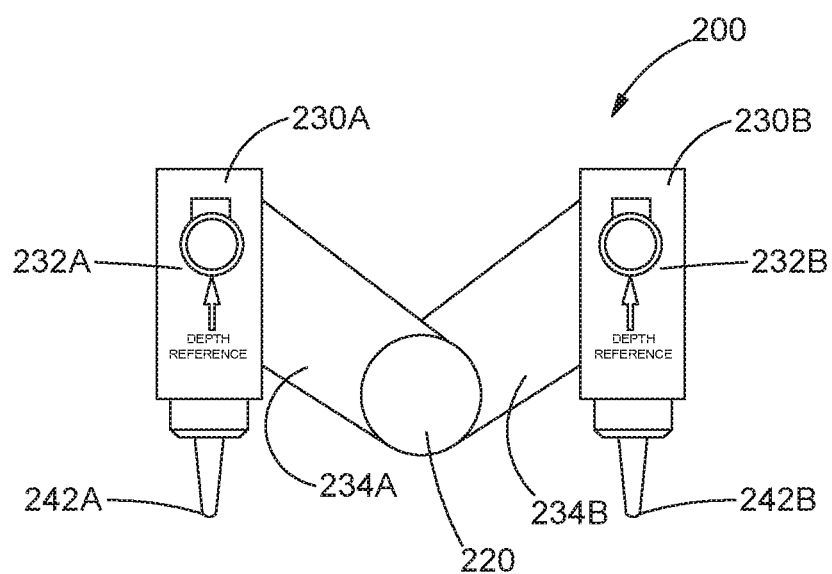
Figure 13:
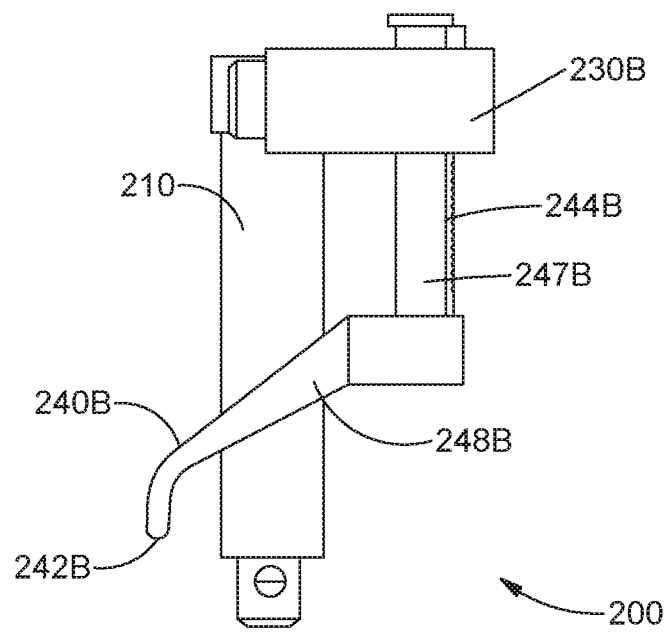

FIGS. 13A-13C show views of an alternative embodiment of an adjustable double tibial stylus 200 configured for use with the tibial resection guide 10. Unlike the translating embodiment shown in FIGS. 1, 2D and 3 and described above, the first and second stylus members 230A, 230B of the embodiment of FIG. 13 are arranged in a pivoting relationship to one another. The first and second stylus members 230A, 230B each include a first/second support member 232A, 232B, respectively. Each stylus support member 232A, 232B has a first/second stylus arm 234A, 234B, respectively, extending therefrom. The stylus arms 234A, 234B are solid along their lengthwise dimensions; instead of a lengthwise groove 236A, 236B, each arm 234A, 234B is provided with a hole adjacent a pivot end thereof, the holes sized to receive an annular neck 224 of a retaining post 220 in a pivoting relationship.

The first and second stylus members 230A, 230B are arranged on opposing sides of a generally centrally positioned tubular body member 210. As in the embodiment shown in FIG. 3, a retaining post 220 extends proximally from the tubular body member 210. The retaining post 220 includes a proximal head 222 and an annular neck 224. In the views of FIG. 13A-13C, the annular neck 224 is obscured by the stylus arms 234A, 234B and is not visible, but the neck 224 can have the configuration of the annular neck 224 shown in FIG. 3. The annular neck 224 is closely sized to fit within the holes on the arms 234A, 234B to thereby provide a pivoting relationship between the arms 234A, 234B and the retaining post 220. Each stylus arm 234A, 234B pivots about the post 210 while being retained on the post by the head 222.

In the translating embodiment described above, each of the tibial stylus members 240A, 240B is substantially straight. In contrast, as shown most clearly in the side view of FIG. 13C, in the pivoting embodiment, each of the tibial stylus members 240A, 240B includes a vertical portion 247A, 247B and a posteriorly lateralized portion 248A, 248B. The vertical portion 247A, 247B selectively translates up-and-down within the support members 232A, 232B. Each of the lateralized portions 248A, 248B terminates in a downwardly depending tip 242A, 242B. The lateralized portions 248A, 248B and tips 242A, 242B are sized and configured to allow the tips 242A, 242B to be positioned on the medial and lateral tibia plateau during pivoting of the arms 234A, 234B.

Each of the first and second support members 232A, 232B includes a cavity for receiving the vertical portions 247A, 247B of the respective first/second adjustable tibial stylus members 240A, 240B therethrough in a substantially proximal-distal orientation. Each tibial stylus member 240A, 240B includes a first/second stop member 241A, 241B, respectively, on a proximal end thereof, and a first/second stylus tip 242A, 242B, respectively, on an opposing distal end thereof. The stylus tips 242A, 242B are configured to selectively abut a tibial articular surface of a patient during use of the instrument assembly 1. Each of the first and second tibial stylus members 240A, 240B is configured to translate proximally/distally within its respective support member 232A, 232B. Selective positioning of the tibial styluses 242A, 242B can be provided by a ratchet mechanism, with ratchet teeth 244 formed on the tibial stylus member 240 between the stop member 241 and the stylus tip 242. A stylus button 250A, 250B is provided on each support member 232A, 232B. The stylus button 250A, 250B is operatively connected to the ratchet teeth 244, such that depressing the stylus button 250A, 250B releases the ratchet teeth 244 for selective repositioning of the tibial stylus member 240 relative to an articular surface of the tibial plateau of a patient. Release of the stylus button 250 locks the tibial stylus member 240A, 240B in position.

Femoral Resection Guide Assembly

Figure 4A:
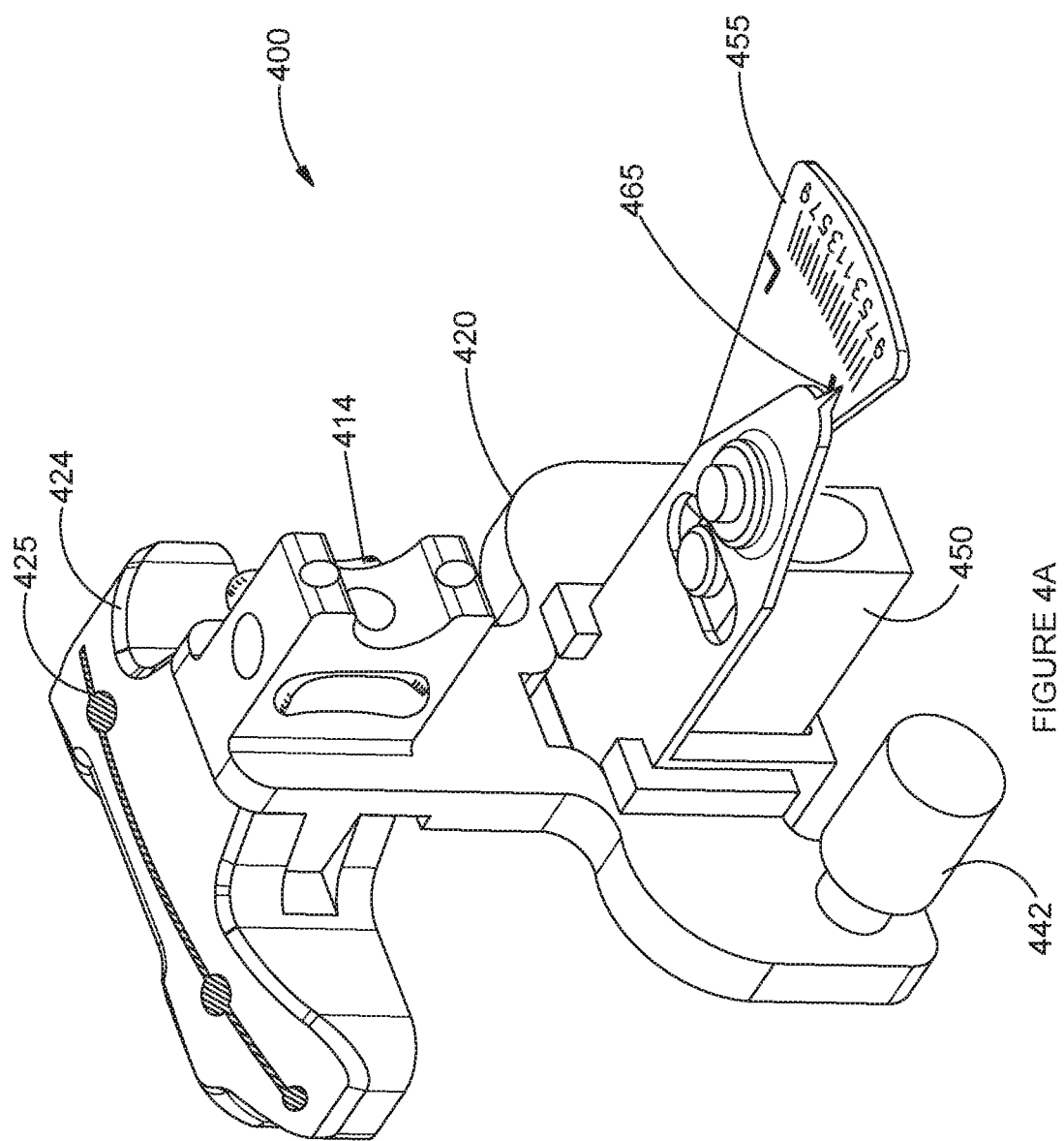
FIG. 4A is a distal perspective view of one embodiment of an assembly for a distal femoral resection guide.
Figure 4B:
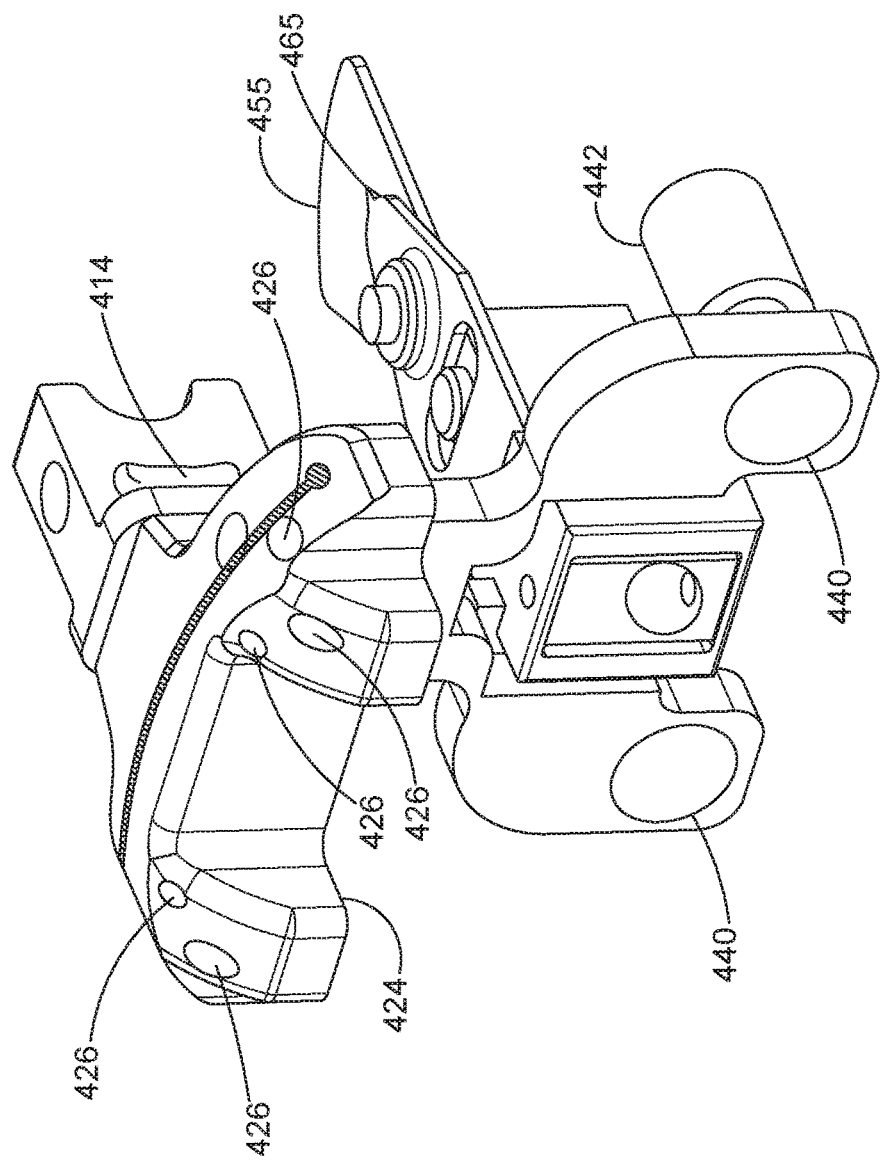
FIG. 4B is a proximal perspective view of one embodiment of an assembly for a distal femoral resection guide.
Figure 4C:
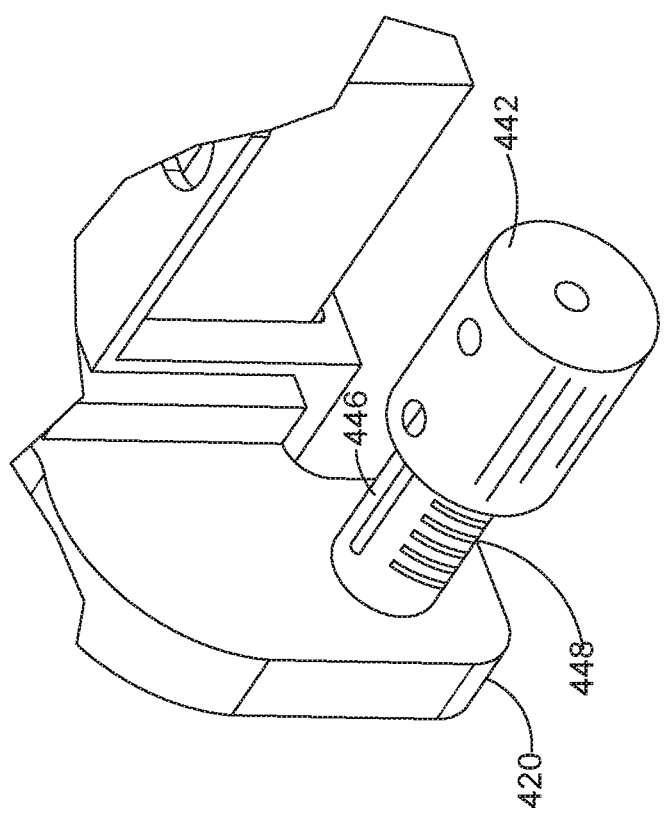
FIG. 4C is a proximal perspective view showing details of one embodiment of an adjustment arrangement for pad members of the invention.

FIGS. 4A, 4B, and 4C provide views of an embodiment of a distal femoral resection guide assembly 400 configured for use with the instrument assembly 1. The femoral resection guide 400 includes a valgus guide body 420 that is adjustably affixed to a stable portion 450, such as an intramedullary (IM) rod holder member 450. The IM rod holder member 450 is configured for selective mounting of the femoral resection guide assembly on an IM rod positioned in a distal femur of a patient, in a manner known to those of skill in the art. The valgus guide body 420 is configured to fixedly receive a femoral distal resection guide 424 on an anterior or upper end thereof for use in resecting the distal femur. The resection guide 424 has a resection slot 425 therethrough for use in receiving a surgical sawblade for making the distal resection of the knee, in a manner known to those of skill in the art. As shown in FIG. 4B, various pin bores 426 allow the resection guide 424 to be selectively pinned to the distal femur of a patient in the position selected through use of the distal femoral resection guide 400. As indicated in FIG. 4A, the valgus guide body 420 is provided with a release button 414 for use in selectively releasing the resection guide 424 from the valgus guide body 420. The valgus guide body 420 can be configured such that the femoral resection guide 424 readily snaps into place on the valgus guide body 420 in a spring-loaded condition and remains secured in place on the valgus guide body 420 until the release button 414 is shifted to a release position.

The valgus guide body 420 is adjustable relative to the IM rod holder member 450 for use in selecting a desired angle of resection. The selected varus/valgus angle may be indicated by a gauge arrangement, such as a pointer 465 formed on a distal end of the femoral valgus guide body 420 and an adjacent degree scale 455 etched or otherwise affixed to a distal area of the IM rod holder member 450. The degree scale 455 may include discrete degree markings over a working range, such as −9 degrees to +9 degrees, in which −9 to 0 degrees corresponds to 9 to zero degrees of rotation of the valgus guide body 420 to the right, while 0 to 9 degrees corresponds to 0 to +9 degrees of rotation of the valgus guide body 420 to the left. Note that in the scale 455 shown in FIG. 4A, the "R" symbol is placed on the left side of the scale 455, while the "L" symbol is placed on the right side of the scale 455, to assist the surgeon in accurately reading the relative reading on the scale 455. The valgus angle module 450 may be modular. The valgus angle may be infinitely variable within the specified range, or may be set to lock at discrete increments, such as 1 degree increments.

The valgus guide body 420 includes adjustment pads 440 that are adjustable relative to the femoral condyles of a patient, such as in 1 mm increments. The adjustment pads 440 may also be referred to as styluses since the medial and lateral pads 440 serve as styluses. FIG. 4C shows details of an embodiment of the adjustment pads 440. As indicated in FIG. 4C, each pad 440 is operatively engaged to an adjustment member 442, such as knob 442. An adjustment pad support member 446 extends distally in a fixed relationship from the valgus guide body 420. An adjustment pad gauge 448 is formed on the adjustment pad support 446 for use in determining the amount of valgus adjustment. For example, the adjustment pad gauge 448 may include indicators for 0, 1, 2, 3, and 4 mm. The adjustment pad knob 442 may be slidingly engaged to the adjustment pad support member 446, such that pushing or pulling the adjustment knob 442 causes the adjustment pad 440 to extend or retract, respectively, relative to the femoral valgus guide body 420. In other embodiments, the adjustment pad knob 442 may be threadibly engaged to the adjustment pad support member 446, such that turning the knob 442 extends or retracts the associated adjustment pad 440. Other arrangements may be used, provided that the adjustment pad 440 remains secured in the desired position during setting of the resection guide 424.

Figure 9D:
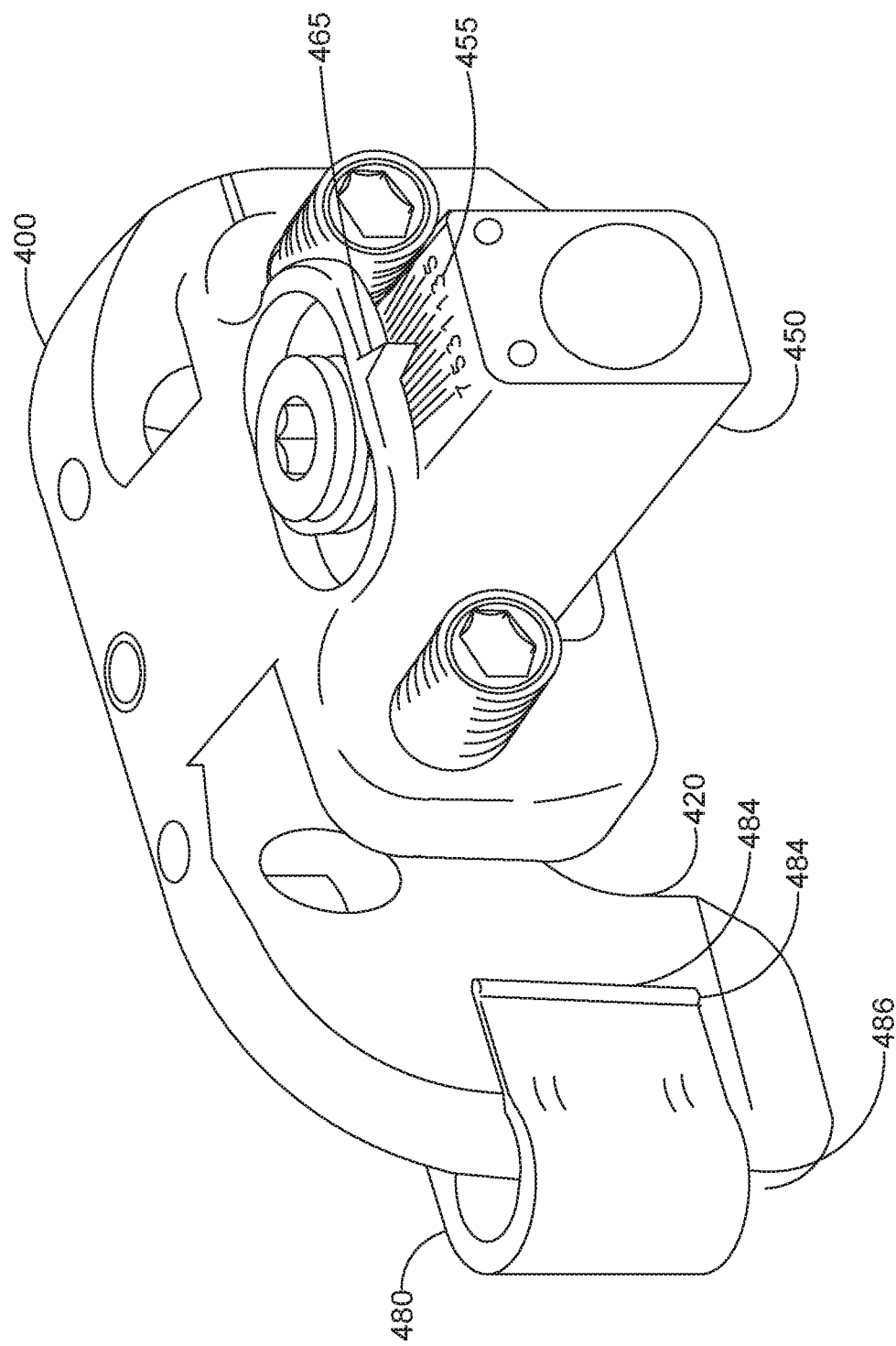
FIG. 9D is a top perspective view of one embodiment of a clip-on spacer shown removably clipped to an embodiment of a distal femoral resection guide.

In alternative embodiments, modular clip-on spacers 480, such as the embodiments shown in FIGS. 9A-9D, can be used in place of adjustment pads 440. FIGS. 9A-9C show views of one embodiment of a unibody modular clip-on spacer 480. FIG. 9D shows a view of a clip-on spacer 480 removably clipped to one embodiment of a distal femoral resection guide 400.

In the side view of FIG. 9A, the clip-on spacer 480 includes a bone side wall 481 for abutting against the distal femur of a patient, and an opposing guide side wall 482 for abutting against an interior proximal back side of the guide 400. The distance between the bone side wall 481 and the guide side wall 482 is a selected distance, such as 2 mm, 3 mm, 4 mm, etc. so as to allow the surgeon to precisely account for a wear factor.

As indicated in FIG. 9A, an opposing clip portion 483 having a release tab 484 is positioned opposite the guide side wall 482. The distance between the opposing clip portion 483 and the guide side wall 482 is selected to be slightly smaller than the thickness of the femoral valgus guide body 420, such that a surgeon can selectively clip the spacer 480 onto the femoral valgus guide body 420 in a secure arrangement, as indicated in FIG. 9D. A proximal bulge 486 assists in biasing the wall 482 and the clip portion 483 toward one another. An interior gap 488 in the bulge 486 area is sized for use in removal of the clip 480 from the guide 400. The release tab 484 is configured for use in opening the clip-on spacer 480 for removal from the guide 400. As indicated in FIGS. 9A and 9D, a proximal bulge 486 can be provided for visualization and for use in pulling the clip-on spacer 480 off of the femoral valgus guide body 420.

Figure 10:
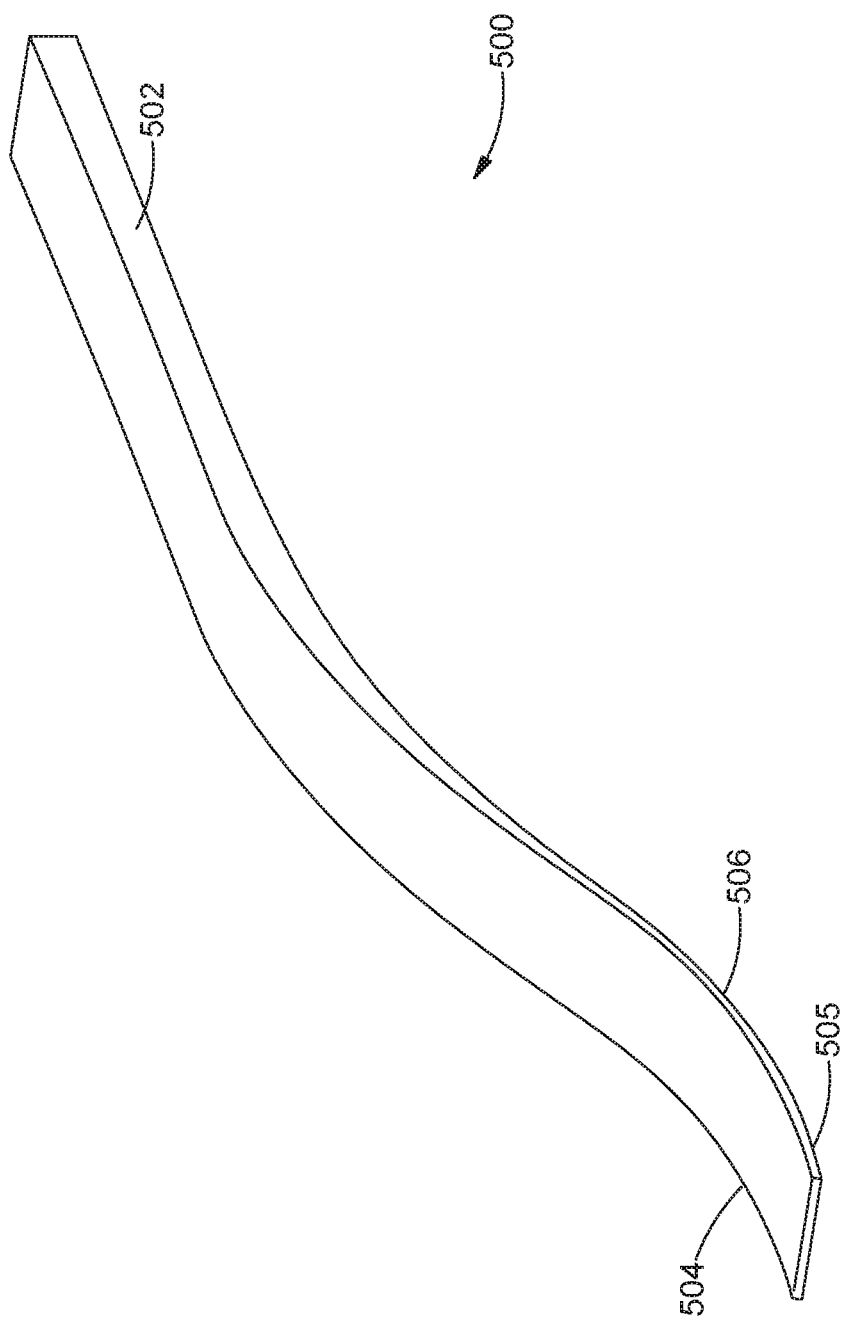
FIG. 10 is a side perspective view of one embodiment of a curved gap spacer gauge instrument of the invention for use in a kinematic alignment technique of the invention.

The curved thickness gauges 500, an exemplary embodiment of which is shown in FIG. 10, allow the surgeon to measure medial and lateral gaps with a femoral trial in place. The medial and lateral gaps can then be used to calculate the medial and lateral resections of the tibia.

Extramedullary Tibial Guide

FIG. 5 provides a side perspective view of one embodiment of an adjustable tibial resection guide 10 functionally attached to a proximal end of an extramedullary (EM) tibial alignment instrument 300. The distal assembly of the EM tibial alignment instrument is conventional in form, and secures the distal end of the instrument around the ankle of a patient in a manner generally known to those of skill in the art. However, a mid-shaft support attachment 330 allows the EM portion of the guide to remain held in place while the tibial resection guide body 20 is allowed to adjust and free float to a desired varus/valgus angle.

Figure 6A:
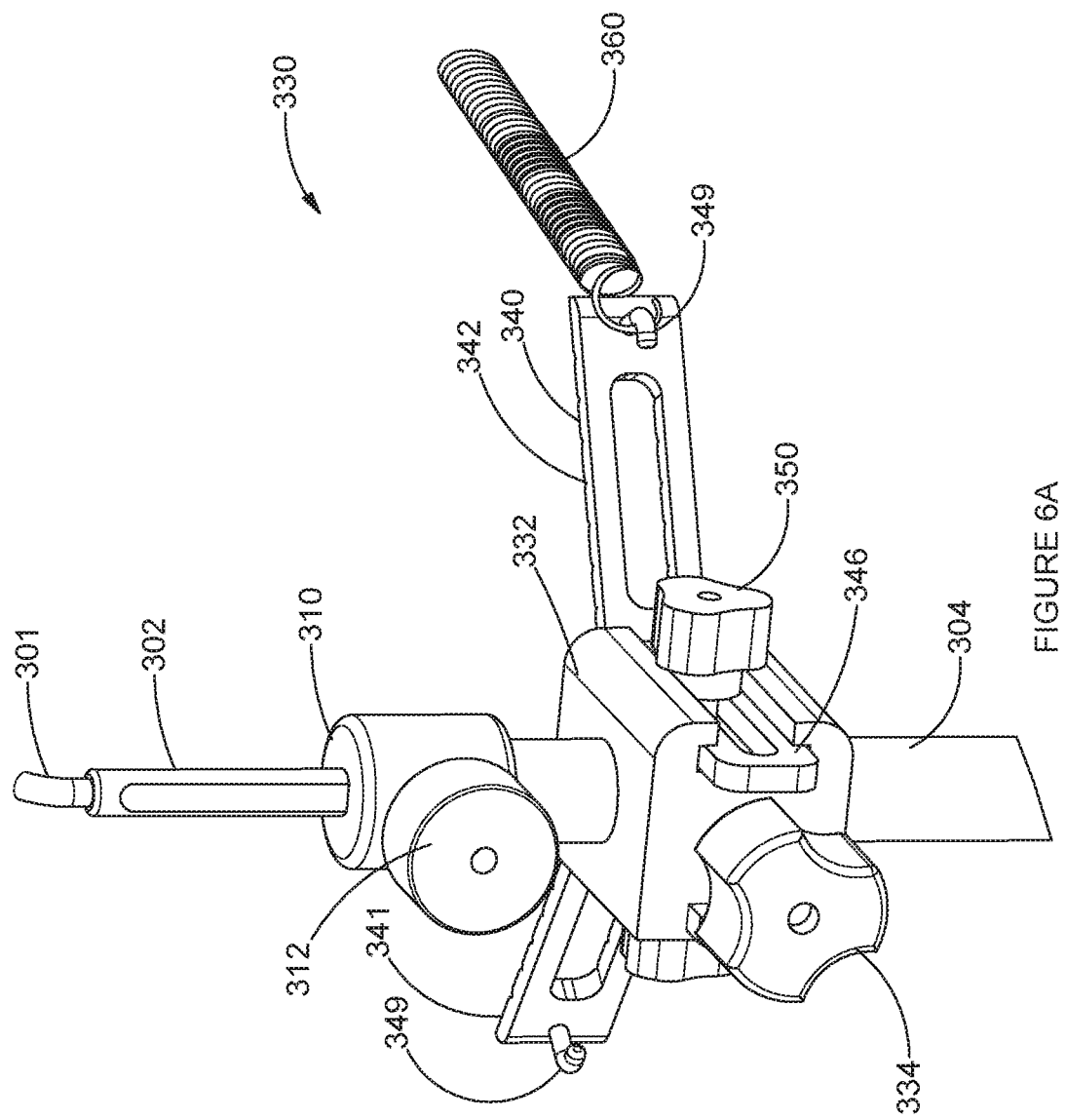
FIG. 6A is a front-side perspective view of one embodiment of a mid-shaft support attachment for an extramedullary tibial alignment instrument of the invention.
Figure 6B:
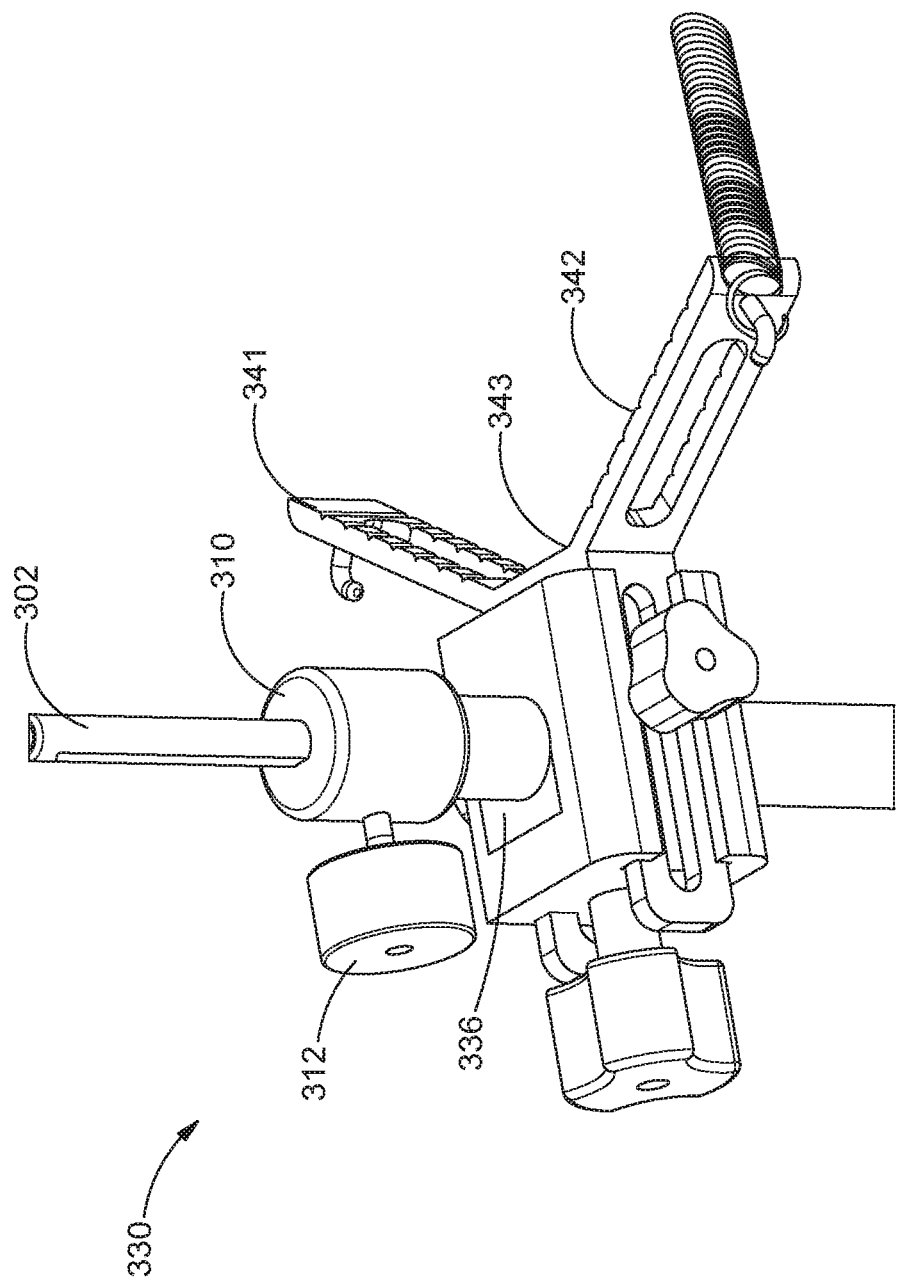
FIG. 6B is a side perspective view showing details of one embodiment of a mid-shaft support attachment for an extramedullary tibial alignment instrument of the invention.

FIGS. 6A and 6B show details of one embodiment of a mid-shaft support arrangement 330 for use with the EM tibial alignment instrument 300. A shaft extension 302 protrudes from a superior shoulder 310 of a primary shaft 304 in a sliding relationship to allow for vertical adjustments in length to accommodate patient size. An adjustment knob 312 is operatively provided for adjusting and selectively locking the length of shaft extension 302 relative to the primary shaft 304. The mid-shaft support attachment 330 is configured to attach to the EM tibial alignment instrument 300 in an adjustable relationship to the primary shaft 304. A support body 332 is configured to generally support the mid-shaft support attachment 330 on the primary shaft 304. A clamp member 336 is provided on an interior of the support body 332. The clamp member is operatively engaged to a vertical adjustment knob 334 for use in clamping the mid-shaft support attachment 330 to the EM primary shaft at a selected vertical orientation. A mid-calf engagement member 340 is slidingly engaged to the support body 332. As shown in FIG. 6B, the mid-calf engagement member 340 includes a first wing 341 and a second wing 342, the wings 341, 342 secured to one another in a fixed relationship by a central spacer portion 343. An anterior-posterior extension member 346 extends from the mid-calf engagement member 340, and is positioned to slidingly engage a positioning groove formed in the support body 332. An anterior-posterior adjustment knob 350 is provided for use in securing the mid-calf engagement member 340 in a selected A-P relationship relative to the patient's calf.

A spring hook 349 is fixed adjacent to an outer end of each of the first and second wing members 341, 342 for use in securing opposing ends of spring member 360 to each of the wings 341, 342, for selectively securing the mid-shaft support attachment 330 on a mid-calf area of a patient. Alternatively an elastic strap, such as of rubber, can be used in place of the spring.

Figure 7A:
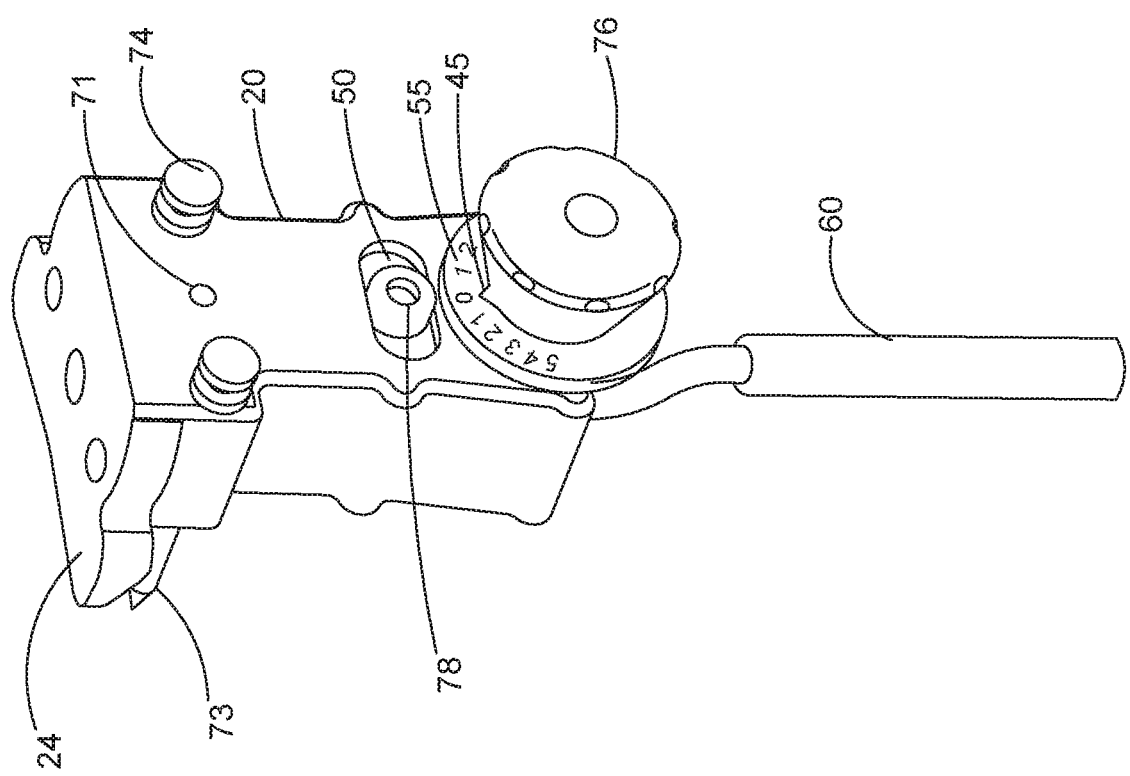
FIG. 7A is a front-side perspective view of one embodiment of an adjustable version of a tibial resection guide that is adjustable to discrete positions via a gear arrangement.
Figure 7B:
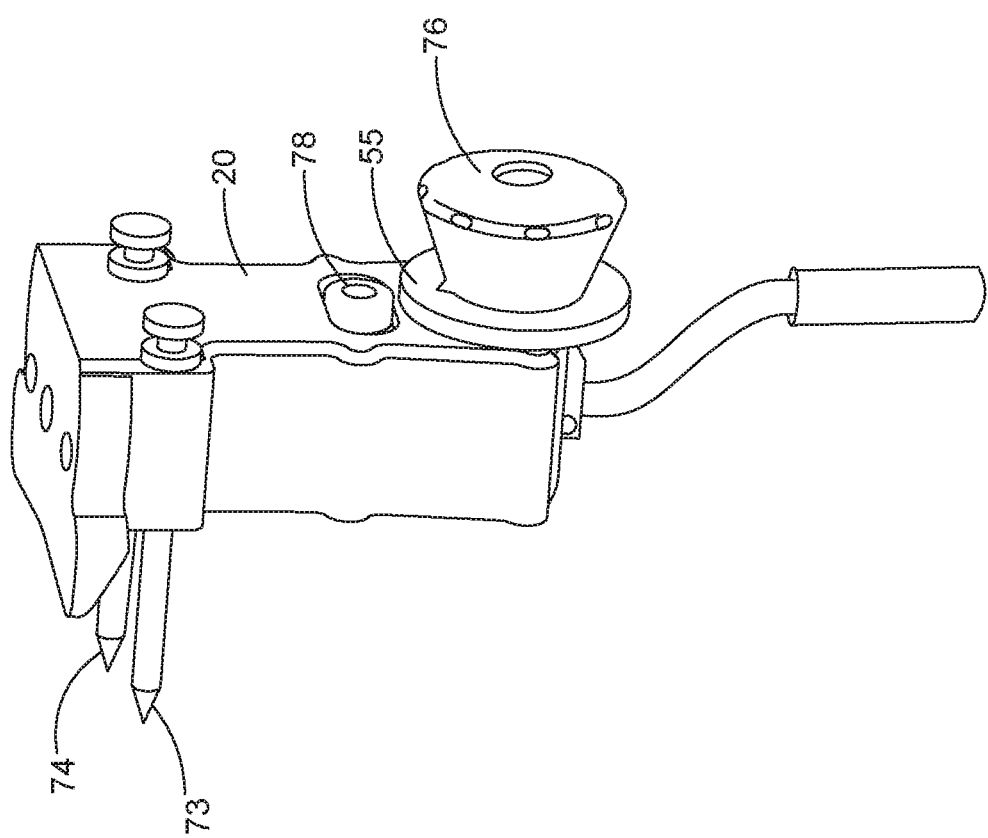
FIG. 7B is a side view of one embodiment of an adjustable version of a tibial resection guide that is adjustable to discrete positions via a gear arrangement.

FIGS. 7A and 7B show views of an alternate dial adjustable EM tibial guide 10 that is adjustable to discrete positions via a gear arrangement. The configuration of the embodiment shown in FIGS. 7A-7B shares features with the embodiment of FIG. 2, but additionally features a unique adjustment and locking mechanism. In the depicted embodiment, the tibial guide support member 50 is substantially enclosed within the resection guide body 20. The adjustment knob 76 is operatively connected to the tibial guide support member 50 via a gear arrangement. In one embodiment, the knob 76 is operatively connected to a geared shaft, the geared shaft having a gear arrangement, such as on a leading end thereof. The geared shaft is disposed such that the gear arrangement engages an opposing gear or rack on the tibial guide support member 50. By turning the knob clockwise or counterclockwise, the surgeon can adjust the varus/valgus angle of the tibial resection guide body 20. The knob 76 is configured to selectively engage and disengage a stop member to set or lock the varus/valgus angle. The knob 76 can be locked at discrete increments, such as 5, 4, 3, 2 or 1 degrees right, 0 degrees, or 1, 2, 3, 4, or 5 degrees left. In one embodiment, the knob 76 is normally in a disengaged position for use in turning the knob 76 to a desired varus/valgus position, and can be depressed or pushed in to engage the stop member to selectively lock the varus/valgus angle.

When using the instruments in a kinematic alignment technique (described in further detail below), the surgeon may find it useful to use a curved thickness gauge 500, an embodiment of which is shown in FIG. 10. The curved thickness gauge 500 includes an elongated handle portion 502 for use by the surgeon in holding and manipulating the instrument 500, an opposing insertion end 504 for insertion into the knee space, and a curved portion 506 extending between the handle portion 502 and the insertion end 504. The curved portion 506 is configured for ease of insertion of the insertion end 504 into the joint space through the incision. The insertion end 504 is sized to a particular thickness 505 for use in measuring the gap. The curved thickness gauge 500 can be provided in varying thicknesses, such as, for example, 1 mm, 2 mm, 3 mm, 4 mm, and 5 mm. The components of the instrument system kit are preferably arranged in a convenient format, such as in a surgical tray or case. However, the kit components do not have to be packaged or delivered together, provided that they are assembled or collected together in the operating room for use at the time of surgery.

Cartilage Thickness Gauge

Figure 14:
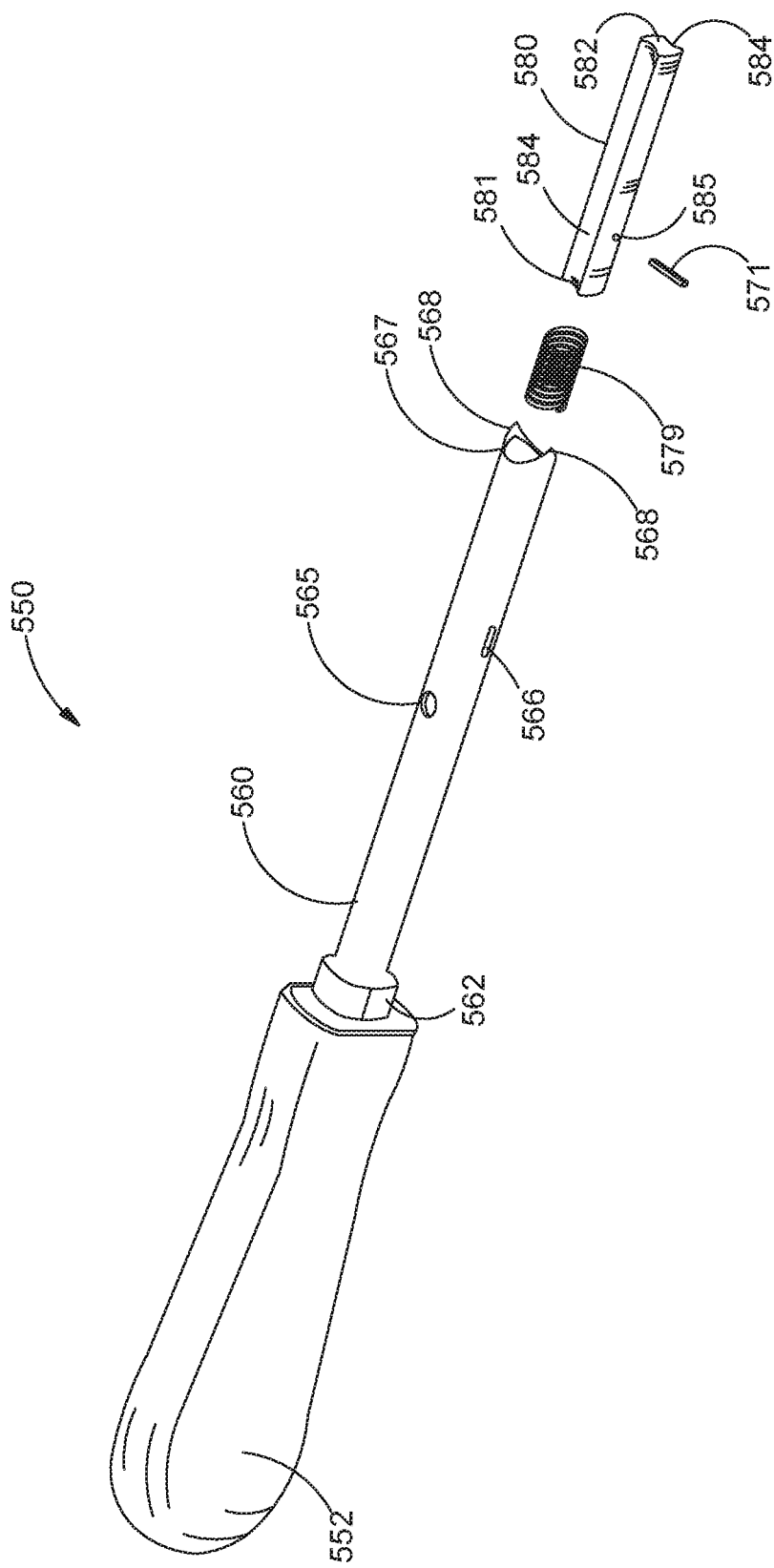
FIG. 14A is a side view of one embodiment of a cartilage thickness gauge.
FIG. 14B is a side view of the cartilage thickness gauge of FIG. 14A, rotated 90 degrees.
FIG. 14C is an exploded view of the cartilage thickness gauge of FIG. 14A.

As shown in FIGS. 14A-14C, a cartilage thickness gauge 550 can be used with the instruments described herein and be included in a kit containing one or more of the foregoing instruments. The cartilage thickness gauge 550 is designed to measure the thickness of the normal cartilage in the knee at the beginning of the procedure. The gauge 550 works by pressing a sharp tip 568 through the cartilage until it is stopped by bone. The thickness of the cartilage can be read by referencing the markings on the side of the gauge 550.

FIGS. 14A-14C show one embodiment of a cartilage thickness gauge 550 configured for use with the instruments and surgical procedures described herein. The cartilage thickness gauge includes a handle portion 552 on a trailing end. An outer shaft portion 560 extends from the handle toward a leading end. The outer shaft portion 560 is configured to attach to the handle, such as via an extension (not shown) that extends into the handle, and a shoulder 562 sized and configure to abut against a leading end of the handle 552. In the embodiment of FIGS. 14A-14C, the shaft portion 560 includes a solid portion 563 and a hollow portion 564. The hollow portion 564 extends from a leading end of the solid portion to leading end of the outer shaft portion 560, thus providing a lengthwise hollow tube inside the leading end of the shaft portion 560. The tube is sized to closely receive a piston 580, as indicated in the exploded view of FIG. 14C.

The hollow portion 564 is provided with features that improve the function of the gauge. These features include opposing cut-outs 567 on the leading end, which form opposing sharps 568. The sharps 568 are sharp enough to readily penetrate knee cartilage, but not the underlying bone. As seen in FIG. 14A, a lengthwise slot 566 extends along the hollow portion 564. Opposing slots 566 can be provided on opposite sides of the shaft 560. Thickness indicia 572, such as millimeter markings, are provided along the slot 566. A sterilization window 565 or opposing sterilization windows 565 can be provided. In the embodiment of FIGS. 14A-14C, the windows 565 are provided on the trailing end of the hollow portion 564.

As seen in FIGS. 14A-14C, a piston 580 is slidingly engaged in the hollow portion 564 of the outer shaft portion 560. The piston 580 has a trailing end 581, which is configured to abut against an end of an interior biasing spring 579, and a leading end 582, which is configured not to penetrate cartilage. The piston 580 is sized to closely fit an interior diameter of the hollow portion 564 in a captured sliding arrangement. As indicated in FIGS. 14A-14C, the piston 580 is sized to extend along most of a length of the hollow portion 564, the length of the piston 580 allowing for the accommodation of the biasing spring 579 between a leading end of the solid portion 563 and a trailing end 581 of the piston 580. The piston 580 is generally circular in cross section but may be provided with opposing lengthwise grooves 584 to improve steam sterilization, as shown in FIG. 14C.

While various means could be used to capture the piston 580 in a captured sliding relationship with the shaft 560, the embodiment of FIGS. 14A-14C provides an arrangement in which a through-pin 571 is used to efficiently provide both a thickness marker 571 and retain the piston 580 in the hollow portion 564 of the shaft 560. As shown in FIG. 14C, the piston 580 is provided with a through-bore 585 sized to receive the pin/thickness marker 571. The through-bore 585 is positioned to allow the pin 571 to slide within the slot 566 in a working range of thickness measurements, such as 0 to 5 mm. When a surgeon presses the sharps 568 through the cartilage of a patient, the cartilage depresses the leading end 582 of the piston 580 toward the handle 552. This in turn moves the pin/marker 571 along the thickness indicia 572. The surgeon reads the location of the pin/marker 571 on the thickness indicia 572, yielding the thickness of the cartilage. When the instrument is removed from the cartilage, the spring 579 bias the piston 580 back into a maximally extended position, with the pin 571 abutting against the leading end of the slot 566 to retain the piston 580 in the hollow portion 564 of the shaft 560.

The instrument set may include a measuring caliper to verify the thickness of the bone that has been resected. Finally, while the exemplary embodiments of the tibial guide 10 include captured pins to hold it to the patient's tibia, in another embodiment the tibial guide 10 could instead define holes for drill pins rather than captured pins.

Methods of Use

In use, the instruments are used to position tibial and femoral resections. Techniques for use of the instruments will now be described.

Mechanical Alignment Technique Utilizing the Dual Stylus/Variable Angle Total Knee Instrumentation The instrumentation can be used for the typical, or traditional, mechanical knee implantation technique by locking the angles at the desired settings. Typically, this is 5 degrees of valgus for the distal femoral resection and 0 degrees for the proximal tibial resection. When used in this manner, the advantage the instrumentation offers over traditional instruments is the ability to measure the amount of bone to be resected on the medial and lateral sides of the femur and tibia since there are dual styli on each guide. Ligament releases may be necessary.

Anatomic Alignment Technique Utilizing the Dual Stylus/Variable Angle Total Knee Instrumentation For the Anatomic Alignment Technique, the goal is to have the Hip-Knee-Ankle Angle be 180 degrees (a straight line) but the joint line be 3 degrees varus (relative to the tibia). The distal femoral angle of resection is determined by pre-operative x-rays. The tibial angle of resection is locked at 3 degrees of varus. Ligament releases may or may not be necessary.

Kinematic Alignment Technique

Below is a summary of primary steps in Kinematic Alignment Technique Utilizing the Dual Stylus/Variable Angle Total Knee Instrumentation.

1. Exposure—A medial parapatellar incision is typically utilized but surgeon preference can be used.

Figure 11A:
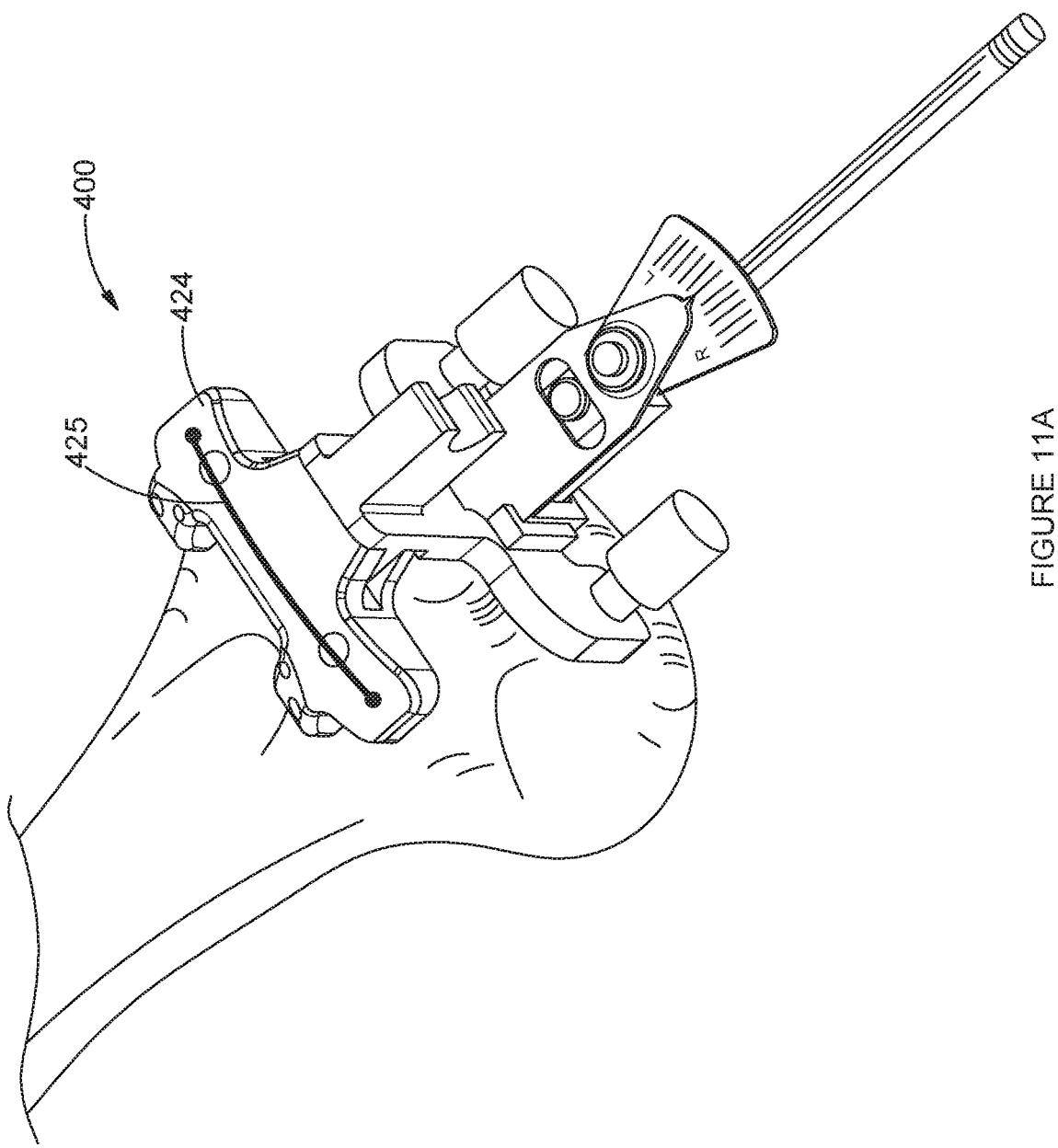
FIG. 11A is a perspective view of one embodiment of a distal femoral resection guide on a distal femur.
Figure 11:
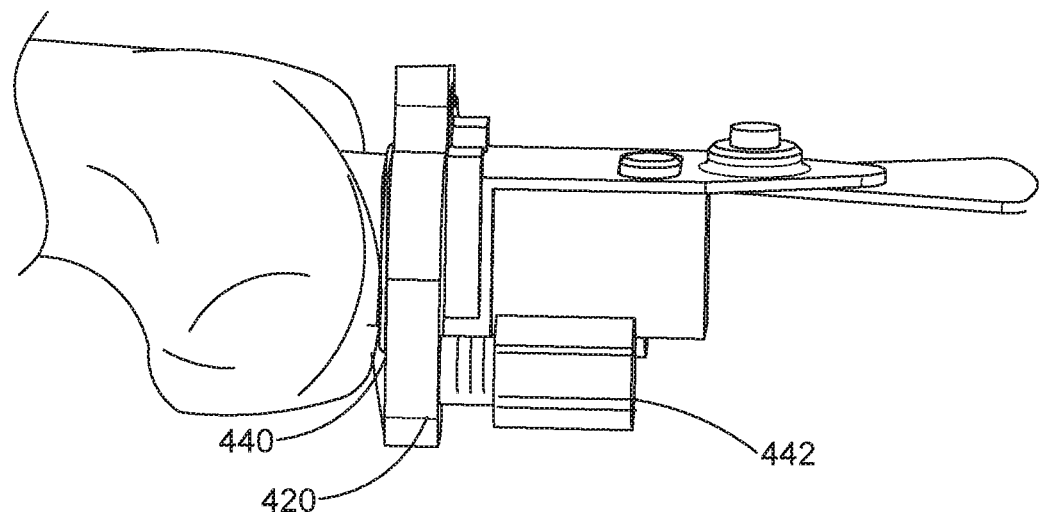
FIG. 11B is a sideview of adjustment of pads of a femoral resection guide against a medial femur.
FIG. 11C is a sideview of adjustment of pads of a femoral resection guide against a lateral femur.
Figure 11:
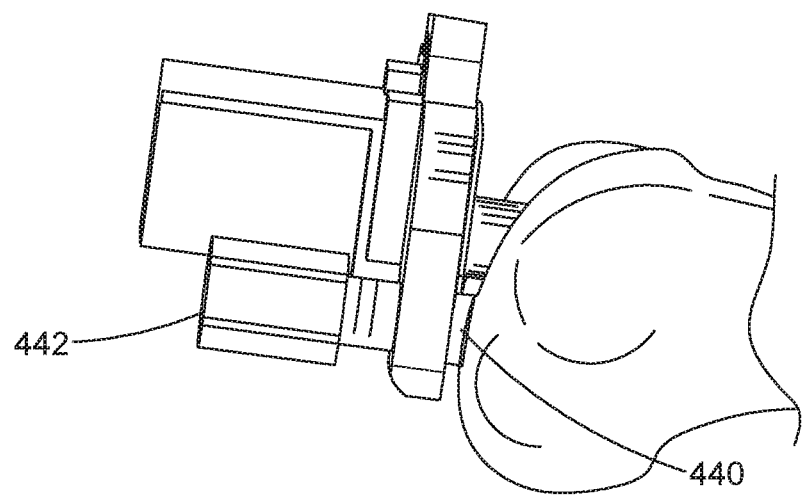

2. Distal Femoral Resection—The cartilage thickness gauge 550 of FIG. 14 can be used at the beginning of the procedure, after the joint is exposed. The surgeon selects an area of cartilage that appears un-worn but close to the area of maximal wear. The cartilage thickness is measured by pressing the cartilage thickness gauge 550 through the cartilage until the sharp tip 568 of the gauge 550 is stopped by bone. This thickness should equal the amount of wear of the area that has full thickness loss of cartilage. The distal femoral resection guide 400 is then adjusted to compensate for that amount of wear on that particular condyle. The measuring procedure: is used on both condyles. As indicated in FIG. 11A, an intramedullary rod is placed into the femur. The femoral guide 400 is placed over the rod. The wear pattern on the distal femur is noted and the adjustable pads 440 (stylus) of the femoral guide 400 are adjusted (FIG. 11B, medial side; FIG. 11C, lateral side). The adjustments are to account for the wear present. Often the wear adjustment is 2 mm on the worn side and 0 mm on the unworn side. As an example, if the medial femur is estimated to have 2 mm wear and the lateral side has 0 mm wear, the medial pad is adjusted to extend 2 mm out from the guide surface. If the desired resection is 10 mm because the femoral implant is 10 mm thick, this will resect 8 mm from the worn medial femur and 10 mm from the lateral femur. This will restore the joint surface to its pre-arthritic level. The guide 400 is positioned to contact the femur medially and laterally and the angle between the guide and the rod is noted. (If it is beyond limits acceptable to the surgeon, the guide can be adjusted.) The cutting guide 424 is pinned to the femur at the selected valgus angle, the femoral guide 400 is removed from the cutting guide 424 and the femur, and the distal femoral cut is made using the pinned cutting guide 424.

3. Setting Femoral Rotation, AP position and Sizing—A posterior referencing sizing guide or sizing caliper is used, in a manner known to those of skill in the art. The rotation is set to zero or aligned to match the AP (anteroposterior) axis of the femur based on surgeon preference (in many cases they may be the same). Size is measured based on AP dimension.

4. Finishing the Femoral Cuts—Once the size is chosen, the appropriate size 4-in-1 cutting block is placed on the distal surface of the femur and the anterior, posterior and chamfer cuts are made, in a manner known to those of skill in the art.

Figure 12A:
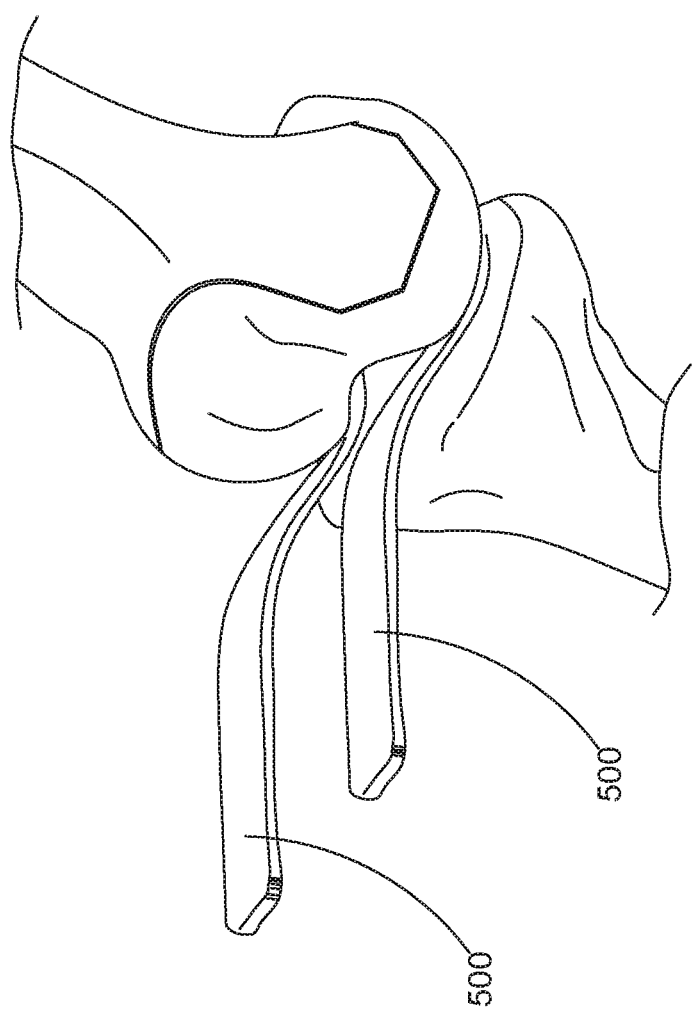
FIG. 12A is a view of use of one embodiment of gap spacer gauges to measure joint space gaps relative to a femoral trial and a natural tibial plateau.
Figure 12:
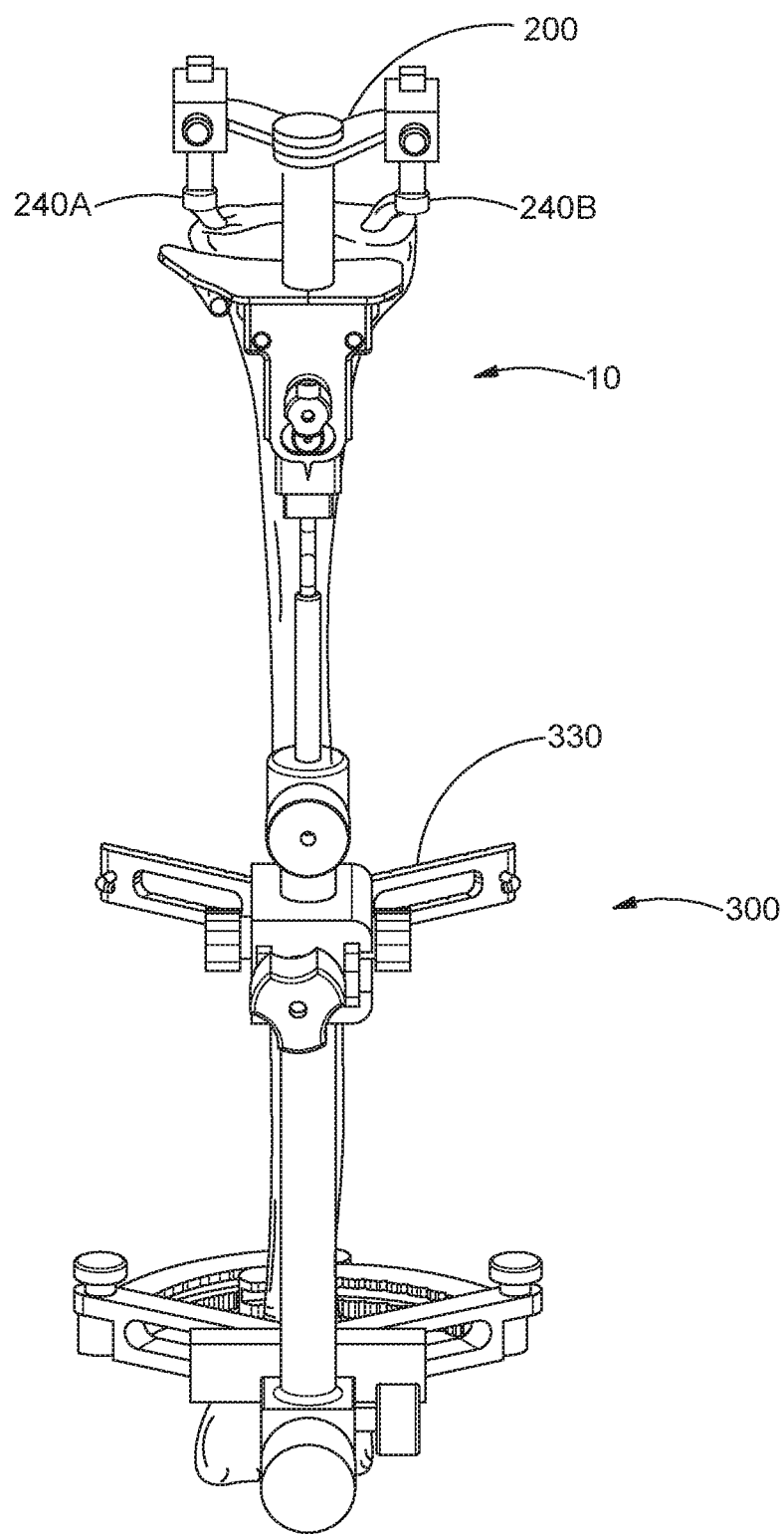
FIG. 12B is a perspective view of one embodiment of an instrument assembly of the invention mounted on a tibia.
FIG. 12C is a perspective view of one embodiment of an adjustable tibial resection guide and an adjustable double tibial stylus mounted on a proximal tibia.
FIG. 12D is a perspective view of one embodiment of an extramedullary tibial alignment instrument mounted on an exterior of a lower portion of a tibia and featuring a view of a mid-shaft support.
FIG. 12E is a perspective view of one embodiment of an adjustable tibial resection guide positioned for use in a tibial resection.
FIG. 12F is a perspective view of one embodiment of an adjustable tibial resection guide configured for use in making larger tibial resection.
Figure 12:
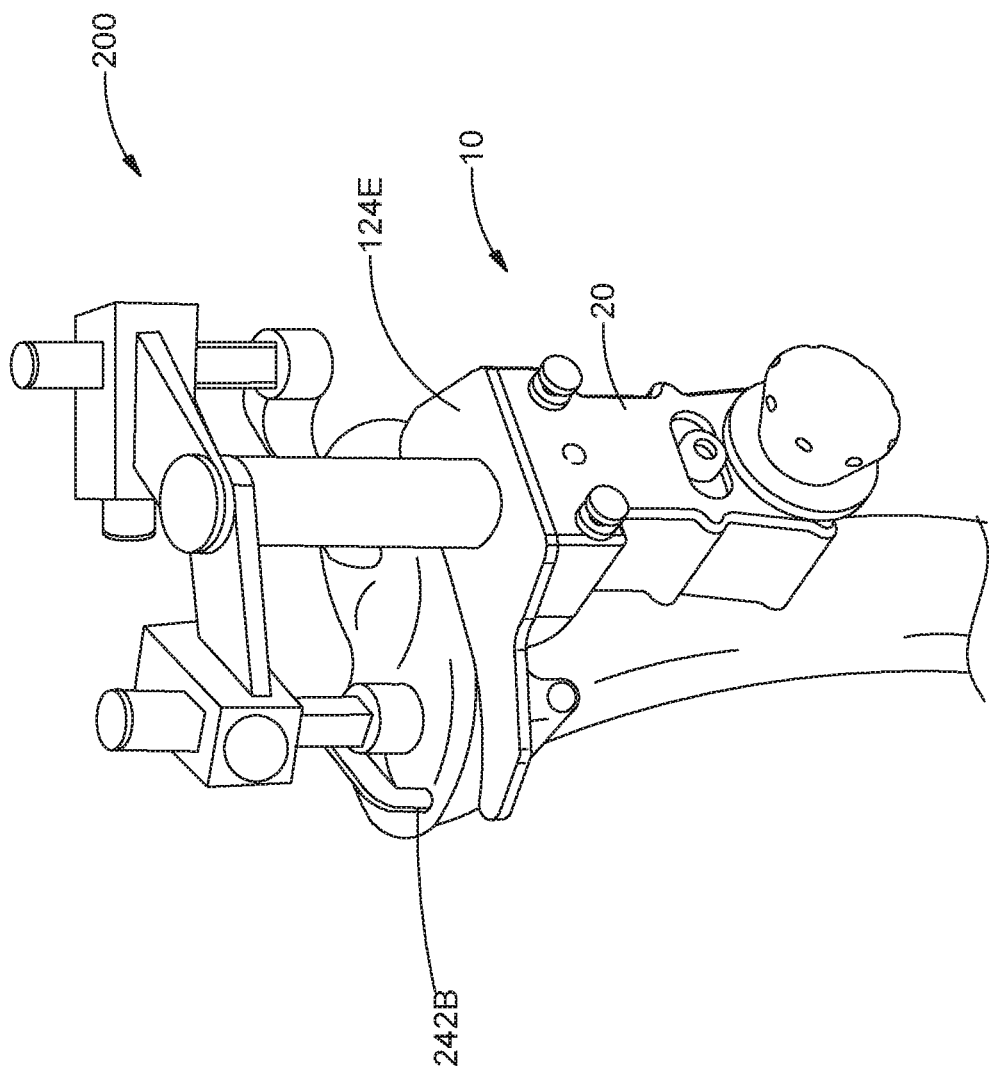
Figure 12:
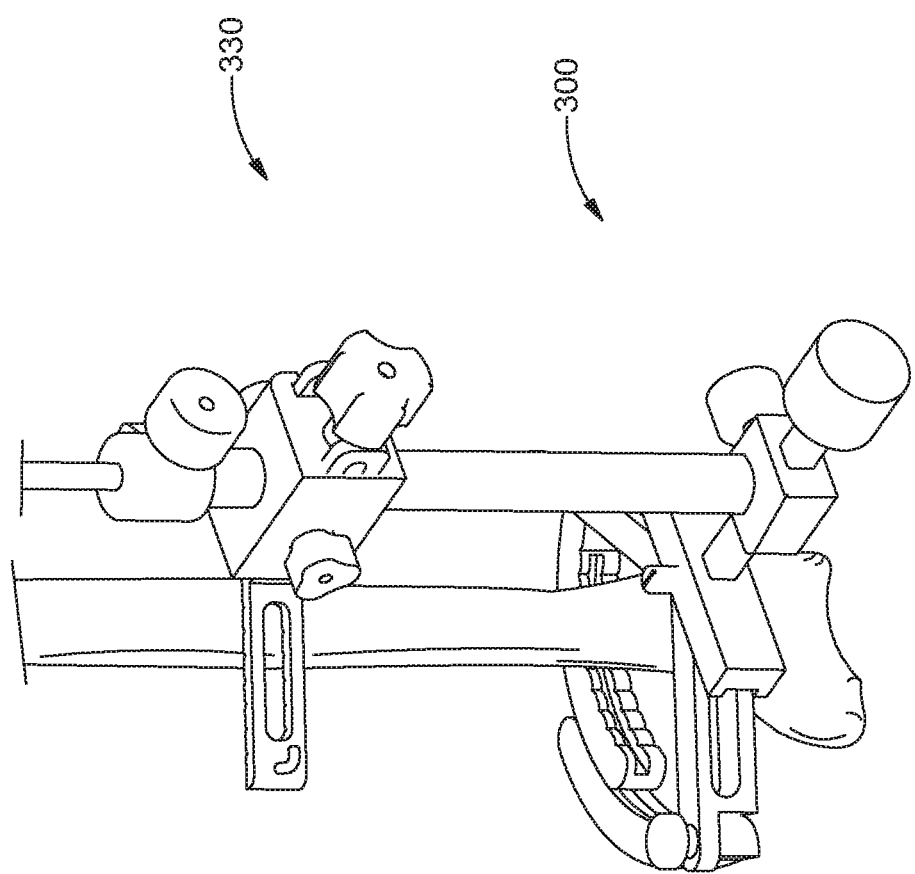
Figure 12:
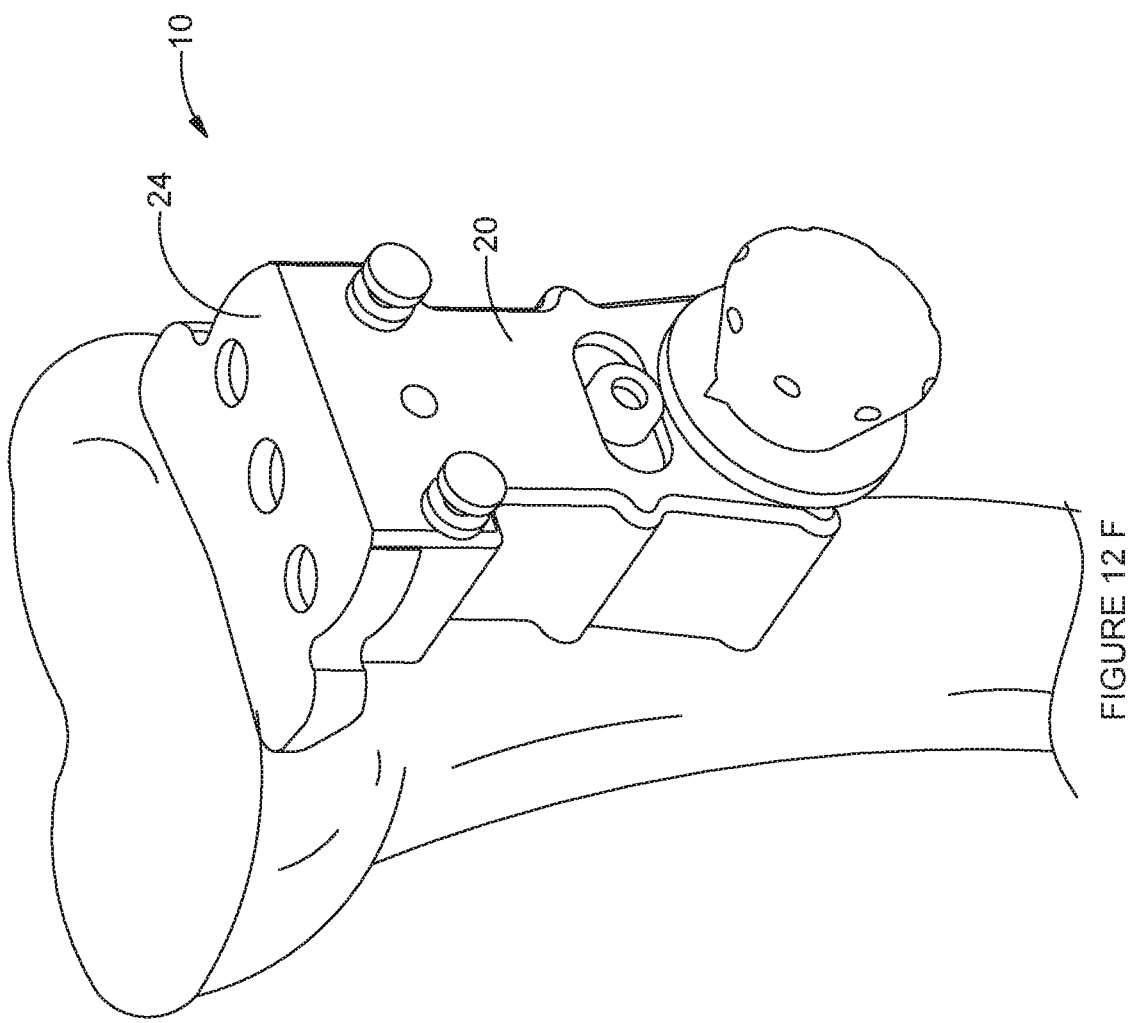

5. Measuring the Gaps—The menisci and ACL are resected. Depending upon surgeon preference and implant being utilized, the PCL may also be resected. The femoral implant trial is placed on the femur (FIG. 12A). With the knee extended, the medial and lateral joint space gaps are measured with the curved thickness gap gauges 500 (FIG. 12A).

6. Proximal Tibial Resection—The amount of resection for medial and lateral tibia is calculated by subtracting the measured gap from the desired thickness of resection. For example, if the surgeon plans to use a 10 mm tibial implant and the medial gap is 4 mm and the lateral gap is 2 mm, the medial stylus will be set to resect 6 mm and the lateral stylus will be set to resect 8 mm. The tibial guide 200 is carefully positioned with each stylus contacting the surface of its respective plateau (FIG. 12B). As indicated in FIG. 12C, the medial and lateral styli 242A, 242B are set to the values determined by use of the gap spacer gauge 500. The tibial varus/valgus angle can be allowed to float or it can be adjusted manually using the adjustment mechanism. FIG. 12D shows details of the mid-shaft clamp 330 when mounted on an exterior of the mid-shaft of tibia, which, together with the conventional ankle clamp, provides stability while adjusting the resection level and the varus/valgus angle of the adjustable tibial resection guide 10. FIG. 12E shows the tibial resection guide body 20 of the adjustable tibial resection guide 10 positioned on and pinned to the proximal tibial for use in making the tibial resection using the tibial resection surface 24 as a guide for a saw blade. FIG. 12F shows how the top plate can be removed to configure the adjustable tibial resection guide 10 for use in making a larger or additional tibial resection (typically, +2 mm). The angle can be noted and adjusted if beyond limits acceptable to the surgeon. The tibial cut is then made.

7. Ligament Balancing—Usually not necessary.

8. Completion—The tibial stem preparation is completed. Patellar resurfacing is performed, if desired. The implants are cemented into place. The final polyethylene insert is chosen and inserted. The wound is closed in layers and the dressing is applied.

The flexibility of these instruments allows a surgeon to implant a knee replacement in a mechanical, anatomic, or kinematic alignment. The instruments facilitate a progression from mechanical to kinematic alignment. Surgeons can start using the instruments for mechanical alignment, since that is likely what they are most familiar with, and then venture into kinematic alignment as they gain familiarity with the instruments.

As can be appreciated from the foregoing discussions, the instruments and methods of the invention have a number of advantages over current systems. For example, the instruments allow the angle of the current joint surface to be measured on both the femur and tibia. The instruments allow a wear factor to be used, so that the bone resection can restore the joint surface to its pre-arthritic level on both the femur and tibia. The instruments allow the surgeon to resect a specific amount of bone from medial and lateral aspects of the joint surface on both the femur and tibia and visualize the angle of resection. The instruments allow the angle of resection to float infinitely, rather than in specific increments, within an acceptable range on both the femur and tibia. The instruments allow the surgeon to selectively lock the angle as desired and measure the resection of the medial and lateral femoral condyles or of the medial and lateral tibial plateau.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. An instrument for setting a position of a resection of a distal femur in a total knee arthroplasty, the instrument comprising:
    a stable portion, the stable portion configured for orientation in a set position relative to said distal femur or a proximal tibia,
    a resection guide portion, the resection guide portion configured to guide a resection path for said resection,
    a resection guide body, the resection guide body associated with the resection guide portion in a fixed orientation,
    the resection guide body pivotally connected to the stable portion, whereby pivoting adjustment of the resection guide body on the stable portion sets resection orientations of the resection guide portion,
    the resection guide body having a lock for selectively locking the resection guide body to the stable portion at a plurality of selectable resection orientations,
    wherein the instrument is configured for resection of said distal femur,
    wherein the stable portion is oriented in the set position by securing the stable portion on an intramedullary rod extending from said distal femur,
    wherein the resection path is provided by a resection slot in the resection guide portion, the resection guide portion configured for fixation to the distal femur and selective detachment from the resection guide body,
    wherein the selective detachment of the resection guide portion is provided by a release button on the resection guide body,
    wherein the resection guide body has a medial adjustment pad and a lateral adjustment pad, each adjustment pad selectively adjustable against said femur to pivot the resection guide body on the stable portion to thereby set the resection guide portion in a selected one of the plurality of resection orientations, and
    a gauge for measuring resection orientations, the gauge comprising the stable portion having a degree scale and the resection guide body having a pointer overlaying the degree scale.

2. The instrument of claim 1, wherein the plurality of selectable resection orientations are indiscrete locations within a working range of resection orientations.

3. The instrument of claim 1, wherein the plurality of selectable resection orientations are discrete locations.

4. The instrument of claim 3, wherein the plurality of selectable resection orientations are indicated by the gauge arrangement.

5. The instrument of claim 1, wherein the degree scale is discrete degree markings over a working range.

6. The instrument of claim 5, wherein the working range includes discrete degree markings at −4, −3, −2, −1, 0, 1, 2, 3 and 4 degrees.

* * * * *